United States Patent
Soltesz et al.

(10) Patent No.: US 6,527,761 B1
(45) Date of Patent: *Mar. 4, 2003

(54) METHODS AND DEVICES FOR OBSTRUCTING AND ASPIRATING LUNG TISSUE SEGMENTS

(75) Inventors: Peter P. Soltesz, San Jose, CA (US); Robert Kotmel, Burlingame, CA (US); Tony Wondka, Mountain View, CA (US); Michael P. Reilly, Southlake, TX (US); Wally S. Buch, Atherton, CA (US)

(73) Assignee: Pulmonx, Inc., Palo Alto, CA (US)

( * ) Notice: Subject to any disclaimer, the term of this patent is extended or adjusted under 35 U.S.C. 154(b) by 47 days.

This patent is subject to a terminal disclaimer.

(21) Appl. No.: 09/699,302

(22) Filed: Oct. 27, 2000

(51) Int. Cl.⁷ .............................................. A61M 35/00
(52) U.S. Cl. ....................................... 604/516; 604/509
(58) Field of Search ........................................ 604/516

(56) References Cited

U.S. PATENT DOCUMENTS

| | | | |
|---|---|---|---|
| 5,972,026 A | 10/1999 | Laufer et al. | |
| 6,083,255 A | 7/2000 | Laufer et al. | |
| 6,174,323 B1 | 1/2001 | Biggs et al. | |
| 6,287,290 B1 * | 9/2001 | Perkins et al. | 604/516 |

FOREIGN PATENT DOCUMENTS

| | | |
|---|---|---|
| EP | 1078601 | 2/2001 |
| WO | WO 98/44854 | 10/1998 |
| WO | WO 99/01076 | 1/1999 |
| WO | WO 99/32040 | 7/1999 |
| WO | WO 99/34741 | 7/1999 |
| WO | WO 99/64109 | 12/1999 |
| WO | WO 00/51510 | 9/2000 |
| WO | WO 00/62699 | 10/2000 |
| WO | WO 01/03642 | 1/2001 |
| WO | WO 01/10314 | 2/2001 |
| WO | WO 01/13839 | 3/2001 |
| WO | WO 01/13908 | 3/2001 |

* cited by examiner

Primary Examiner—Teresa Walberg
Assistant Examiner—Leonid M Fastovsky
(74) Attorney, Agent, or Firm—Townsend and Townsend and Crew LLP

(57) ABSTRACT

Methods, systems, devices and kits for performing lung volume reduction in patients suffering from chronic obstructive pulmonary disease or other conditions using and comprising minimally invasive instruments introduced through the mouth (endotracheally) to isolate a target lung tissue segment from other regions of the lung and reduce lung volume. Isolation is achieved by deploying an obstructive device in a lung passageway leading to the target lung tissue segment. Once the obstructive device is anchored in place, the segment can be aspirated through the device. This may be achieved by a number of methods, including coupling an aspiration catheter to an inlet port on the obstruction device and aspirating through the port. Or, providing the port with a valve which allows outflow of gas from the isolated lung tissue segment during expiration of the respiratory cycle but prevents inflow of air during inspiration. In addition, a number of other methods may be used. The obstructive device may remain as an implant, to maintain isolation and optionally allow subsequent aspiration, or the device maybe removed at any time.

68 Claims, 20 Drawing Sheets

METHODS AND DEVICES FOR OBSTRUCTING AND ASPIRATING LUNG TISSUE SEGMENTS

CROSS-REFERENCES TO RELATED APPLICATIONS

The disclosure of this application is related to copending application Ser. No. 09/699,313, filed on the same day, the full disclosure of which is incorporated herein by reference.

BACKGROUND OF THE INVENTION

1. Field of the Invention

The present invention relates generally to medical methods, systems, and kits. More particularly, the present invention relates to methods and apparatus for effecting lung volume reduction by aspirating isolated segments of lung tissue.

Chronic obstructive pulmonary disease is a significant medical problem affecting 16 million people or about 6% of the U.S. population. Specific diseases in this group include chronic bronchitis, asthmatic bronchitis, and emphysema. While a number of therapeutic interventions are used and have been proposed, none are completely effective, and chronic obstructive pulmonary disease remains the fourth most common cause of death in the United States. Thus, improved and alternative treatments and therapies would be of significant benefit.

Of particular interest to the present invention, lung function in patients suffering from some forms of chronic obstructive pulmonary disease can be improved by reducing the effective lung volume, typically by resecting diseased portions of the lung. Resection of diseased portions of the lungs both promotes expansion of the non-diseased regions of the lung and decreases the portion of inhaled air which goes into the lungs but is unable to transfer oxygen to the blood. Lung reduction is conventionally performed in open chest or thoracoscopic procedures where the lung is resected, typically using stapling devices having integral cutting blades.

While effective in many cases, conventional lung reduction surgery is significantly traumatic to the patient, even when thoracoscopic procedures are employed. Such procedures often result in the unintentional removal of healthy lung tissue, and frequently leave perforations or other discontinuities in the lung which result in air leakage from the remaining lung. Even technically successful procedures can cause respiratory failure, pneumonia, and death. In addition, many older or compromised patients are not able to be candidates for these procedures. For these reasons, it would be desirable to provide improved methods, systems, and kits for performing lung volume reduction which overcome at least some of the shortcomings noted above.

2. Description of the Background Art

WO 99/01076 and corresponding U.S. Pat. No. 5,957,919 describes devices and methods for reducing the size of lung tissue by applying heat energy to shrink collagen in the tissue. In one embodiment, air may be removed from a bleb in the lung to reduce its size. Air passages to the bleb may then be sealed, e.g., by heating, to fix the size of the bleb. WO 98/48706 describes a plug-like device for placement in a lung air passage to isolate a region of lung tissue, where air is not removed from the tissue prior to plugging. WO 98/49191 describes the use of surfactants in lung lavage for treating respiratory distress syndrome. U.S. Pat. No. 5,925,060 may also be of interest.

Patents and applications relating to lung access, diagnosis, and treatment include U.S. Pat. Nos. 5,957,949; 5,840,064; 5,830,222; 5,752,921; 5,707,352; 5,682,880; 5,660,175; 5,653,231; 5,645,519; 5,642,730; 5,598,840; 5,499,625; 5,477,851; 5,361,753; 5,331,947; 5,309,903; 5,285,778; 5,146,916; 5,143,062; 5,056,529; 4,976,710; 4,955,375; 4,961,738; 4,958,932; 4,949,716; 4,896,941; 4,862,874; 4,850,371; 4,846,153; 4,819,664; 4,784,133; 4,742,819; 4,716,896; 4,567,882; 4,453,545; 4,468,216; 4,327,721; 4,327,720; 4,041,936; 3,913,568 3,866,599; 3,776,222; 3,677,262; 3,669,098; 3,542,026; 3,498,286; 3,322,126; WO 95/33506, and WO 92/10971.

Lung volume reduction surgery is described in many publications, including Becker et al. (1998) Am. J. Respir. Crit. Care Med. 157:1593–1599; Criner et al. (1998) Am. S. Respir. Crit. Care Med. 157:1578–1585; Kotloff et al. (1998) Chest 113:890–895; and Ojo et al. (1997) Chest 112:1494–1500.

The use of mucolytic agents for clearing lung obstructions is described in Sclafani (1999) AARC Times, January, 69–97. Use of a balloon-cuffed bronchofiberscope to reinflate a lung segment suffering from refractory atelectasis is described in Harada et al. (1983) Chest 84:725–728.

SUMMARY OF THE INVENTION

The present invention provides improved methods, systems, devices and kits for performing lung volume reduction in patients suffering from chronic obstructive pulmonary disease or other conditions where isolation of a lung segment or reduction of lung volume is desired. The present invention is likewise suitable for the treatment of bronchopleural fistula. The methods are minimally invasive with instruments being introduced through the mouth (endotracheally) and rely on isolating the target lung tissue segment from other regions of the lung. Isolation is achieved by deploying an obstructive device in a lung passageway leading to the target lung tissue segment. Once the obstructive device is anchored in place, the segment can be aspirated through the device. This may be achieved by a number of methods, including coupling an aspiration catheter to an inlet port on the obstruction device and aspirating through the port. Or, providing the port with a valve which allows outflow of gas from the isolated lung tissue segment during expiration of the respiratory cycle but prevents inflow of air during inspiration. In addition, a number of other methods may be used. The obstructive device may remain as an implant, to maintain isolation and optionally allow subsequent aspiration, or the device may be removed at any time. Likewise, the device may biodegrade over a period of time.

The obstruction device may take a variety of forms to allow delivery, deployment and anchoring in a lung passageway. Delivery is commonly performed with the use of a minimally invasive device, such as a flexible bronchoscope or an access catheter. The flexible bronchoscope may be utilized with a sheath having an inflatable cuff disposed near its distal end, a full description of which is provided in co-pending application Ser. No. 09/699,313, assigned to the assignee of the present invention and incorporated by reference for all purposes. When using such a sheath, the scope is introduced into a lumen in the sheath to form an assembly which is then introduced to the lung passageway. The cuff may then be inflated to occlude the passageway. Similarly, an access catheter may be used which may be steerable or articulating, may include an inflatable balloon cuff near its distal end and may include a number of lumens for balloon inflation, tracking over a guidewire, and optical imaging, to name a few. The obstruction device is typically housed within a lumen of the access catheter, bronchoscope, sheath or suitable device, mounted near the distal tip of the catheter or carried by any method to the desired lung passageway leading to the target lung tissue segment. Therefore, the obstruction device must be sized appropriately for such delivery and is typically designed to expand upon deployment to anchor within the lung passageway. Hereinafter the present invention is depicted in relation to use with an access catheter, however it may be appreciated that any suitable device may be used.

In a first aspect of the present invention, the obstruction device comprises a structural support which expands and thereby anchors the device in the lung passageway. Such supports may comprise a number of configurations for a variety of expansion techniques. For example, the structural supports may allow the obstruction device to coil, roll, bend, straighten or fold in a cone, rod, cylinder or other shape for delivery. Then, once positioned in a desired location, the obstruction device may be released and expanded to anchor the device in the passageway. Such expansion may be unaided, such as in the release of a compressed structure to a pre-formed expanded position. Or, such expansion may be aided, such as with the use of an inflatable balloon or cuff. In some cases, a balloon or inflatable member may be incorporated into the obstruction device and may remain inflated to occlude the passageway. This may be provided in combination with structural supports or an inflatable balloon or similar device may be used without such support.

The structural supports may be comprised of any type of wire, particularly superelastic, shape-memory or spring tempered wire, or any type of polymer or a suitable material. The balloon or inflatable member may be comprised of any flexible, polymeric material suitable for such a purpose. The member may be inflated with gas or liquid as desired, or it may be inflated with an expanding foam or similar material. Likewise, it may be inflated or injected with an adhesive. Such an adhesive may expand the member and/or rigidify the member to reduce the likelihood of collapse. Further, the adhesive may additionally serve to bond the device to the walls of the lung passageway to increase anchorage. In addition, the device may be impregnated or coated with an antibiotic agent, such as silver nitrate, or similar agent for delivery of the agent to the lung passageway. Such delivery may occur by any applicable means.

When structural supports are present, such supports may comprise a variety of designs. In a first embodiment, the structural supports comprise radial segments which expand to fill the passageway and longitudinal segments which rest against the walls of the passageway to help anchor the device. In a second embodiment, the structural supports comprise a mesh which expands to fill the passageway. In a third embodiment, the structural supports comprise a helically or spirally wound wire which also expands to contact the walls of the passageway and anchor the device. In each of these embodiments, the structural support may be connected with or encapsulated in a sack comprised of a thin polymeric film, open or closed cell foam or other suitable material to provide a seal against walls of the lung passageway and obstruct airflow through the device. The sack material may also be infused with an adhesive, sealant or other material to improve obstruction of the airway and possibly improve adhesion to the airway walls.

In a second aspect of the present invention, the obstruction device may further comprise ports for aspiration through the device. This may allow access to the collapsed lung segment at a later time, for example, in the case of an infection. Typically, the obstruction device will have an inlet port located near the proximal end of the device, away from the isolated lung tissue segment. Such a port is thus accessible by minimally invasive devices, such as an aspiration catheter, which may be advanced through the bronchial passageways. Optionally, an outlet port may be located near the distal end of the obstruction device. The ports may comprise a variety of designs for a number of purposes.

In a first embodiment, the port comprises a self-sealing septum. Such a septum may comprise a solid membrane or a pre-cut membrane. Aspiration through the port may be achieved with the use of an aspiration catheter having an access tube or penetrating element at its distal end. Such a catheter may be advanced to the site of the obstruction device itself or with the use of an access catheter. The septum may be penetrated, either pierced through a solid membrane or passed through the cuts of a pre-cut membrane, by the access tube. Depending on the design of the obstruction device, the inlet port and optionally the outlet port may be penetrated in this fashion. Aspiration may be achieved through the access tube and aspiration catheter to withdraw gases and/or liquids from the isolated lung tissue segment and passageway. Optionally, prior to aspiration, a 100% oxygen, Helium-Oxygen mixture or low molecular weight gas washout of the lung segment may be performed by introducing such gas through the access tube, such as by a high frequency jet ventilation process. In this case, aspiration would remove both the introduced gas and any remaining gas. Similarly, liquid perfluorocarbon or certain drugs, such as antibiotics, retinoic acid and hyaluronic acid, may be introduced prior to aspiration. In most cases, aspiration will at least partially collapse the lung segment. Upon removal of the aspiration catheter from the port, the septum may self-seal or it may be further sealed with a sealant or other sealing means for later access or permanent closure.

When the self-sealing septum comprises a pre-cut membrane, aspiration through the port may alternatively be achieved by coupling an aspiration catheter to the obstructive device. Coupling may comprise engaging the aspiration catheter to the port or sliding a coupling member or the aspiration catheter over the port to form a seal. In either case, suction through the aspiration catheter may allow gases and/or liquids to pass through the cuts in the membrane to be withdrawn from the isolated lung tissue segment and passageway. Again, this will at least partially collapse the lung segment. Likewise, upon removal of the aspiration catheter from the port, the septum may self-seal or it may be further sealed with a sealant or other sealing means for later access or permanent closure.

In a second embodiment, the port comprises a unidirectional valve. Such a valve may comprise a port covered by a flexible layer which is attached to the port by at least one point of connection. Movement of the layer away from the port opens the valve and movement against the port closes the valve. Wherein the flexible layer is solid, movement of the layer away from the port allows gas to flow between the points of connection and around the edges of the flexible layer. Alternatively, the flexible layer may have holes therethrough. In this case, the port may also comprise a partition having holes which are not aligned with the holes in the flexible layer. Movement of the layer away from the port allows gas to flow through the holes in the partition and out through the holes in the flexible layer. When the layer moves against the partition, the holes will be covered closing the valve. Other valve designs include a spring-loaded ball valve or a biased pre-loaded diaphragm valve.

Aspiration through a unidirectional valve may be achieved by a number of methods. Again, the port may be accessed by advancing an aspiration catheter or similar device through the bronchial passageways to the site of the obstruction device. This may optionally be achieved with the use of an access catheter. The aspiration catheter may be placed near the valve or engaged to the valve, wherein suction or vacuum applied through the catheter opens the valve. If the aspiration catheter is not engaged to the valve, adequate suction to open the valve may be achieved by occluding the passageway proximal to the point of suction which is typically the distal end of the aspiration catheter. Such occlusion may be achieved by inflating a balloon or occlusion device mounted on the distal end of the aspiration catheter or mounted on an access catheter. In either case, the vacuum may draw the flexible layer away from the port, allowing gases and/or liquids to flow out from the isolated lung segment, through the valve and into the aspiration catheter. Alternatively, aspiration through a unidirectional valve may be achieved naturally during respiration. Pressure changes may open the valve during expiration as gases flow out from the isolated lung segment. Reverse pressure changes, during inspiration, may close the valve preventing gases from flowing into the isolated segment. This may reduce the amount of gas trapped in the terminal segment over time and thus at least partially collapse the lung segment. Similarly, aspiration through the unidirectional valve may be achieved by external mechanical pressure on the lung to force out of the lung segment and through the valve. Again, reverse pressure changes upon recoil of the lung would close the valve preventing gases from flowing into the isolated segment.

In a third aspect of the present invention, the obstruction device may comprise a blockage device which is deployed in a lung passageway to close the airway. Such a blockage device may be of similar design as previously described obstruction devices as it may be similarly delivered, deployed and anchored within a lung passageway. Thus, embodiments of the blockage device typically comprise expandable support structures. For example, in one embodiment the support structure comprises a coil. And, in a second embodiment, the support structure comprises a mesh. Again, the support structures may be connected to or encased in a polymer film or sack to provide a seal against the walls of the lung passageway and obstruct airflow through the device. Typically the blockage device will be placed in the passageway after the terminal lung segment has been aspirated by other methods. This will seal off the lung segment and maintain lung volume reduction. Alternatively, the blockage device may be placed in the passageway before the terminal lung segment has been aspirated. In this case, air trapped in the lung segment may be absorbed over time and would eventually collapse, a process known as absorption atelectasis. This process may be enhanced by insufflating the lung segment with 100% oxygen, a Helium-Oxygen mixture or low molecular weight gas prior to placing the blockage device. Such enhancement may promote complete collapse of the lung segment. In any case, the blockage device may optionally be later removed if it is so desired.

Methods of the present invention include the utilization of an obstruction device to achieve lung volume reduction. As described above, methods include delivery, deployment and anchoring of an obstruction device in a lung passageway leading to a target lung tissue segment. At least partial collapse of the terminal lung tissue segment may be achieved by aspirating the segment through the obstruction device deployed in the passageway. Aspiration may be accomplished with the use of an aspiration catheter or similar device through a port on the obstruction device. Also described above, when the port comprises a unidirectional valve, aspiration and eventual lung volume reduction may be accomplished by the opening and closing of the valve in response the respiratory cycle. In addition, methods of the present invention include deployment of a blockage device in a lung passageway leading to a terminal lung tissue segment, as previously described.

Systems of the present invention may include any of the components described in relation to the present invention. A particular embodiment of a system of the present invention comprises an access catheter and an obstruction device, as described above, wherein the obstruction device is introduceable by the access catheter. For example, the obstruction device may be houseable within a lumen of the access catheter for deployment out the distal end of the catheter, or the obstruction device may be mountable on the access catheter near its distal end. In either case, the obstruction device may be deployed and anchored within a lung passageway.

The methods and apparatuses of the present invention may be provided in one or more kits for such use. The kits may comprise an obstruction device deployable within a lung passageway and instructions for use. Optionally, such kits may further include any of the other system components described in relation to the present invention and any other materials or items relevant to the present invention.

Other objects and advantages of the present invention will become apparent from the detailed description to follow, together with the accompanying drawings.

DESCRIPTION OF THE SPECIFIC EMBODIMENTS

Lung volume reduction is performed by collapsing a target lung tissue segment, usually within lobar or sub-lobular regions of the lung which receive air through a single lung passage, i.e., segment of the branching bronchus which deliver to and receive air from the alveolar regions of the lung. Such isolated lung tissue segments are first isolated and then collapsed by aspiration of the air (or other gases or liquids which may be present) from the target lung tissue segment. Lung tissue has a very high percentage of void volume, so removal of internal gases can reduce the lung tissue to a small percentage of the volume which it has when filly inflated, i.e. inflated at normal inspiratory pressures. The exemplary and preferred percentages for the volume reduction are set forth above.

Figure 1:
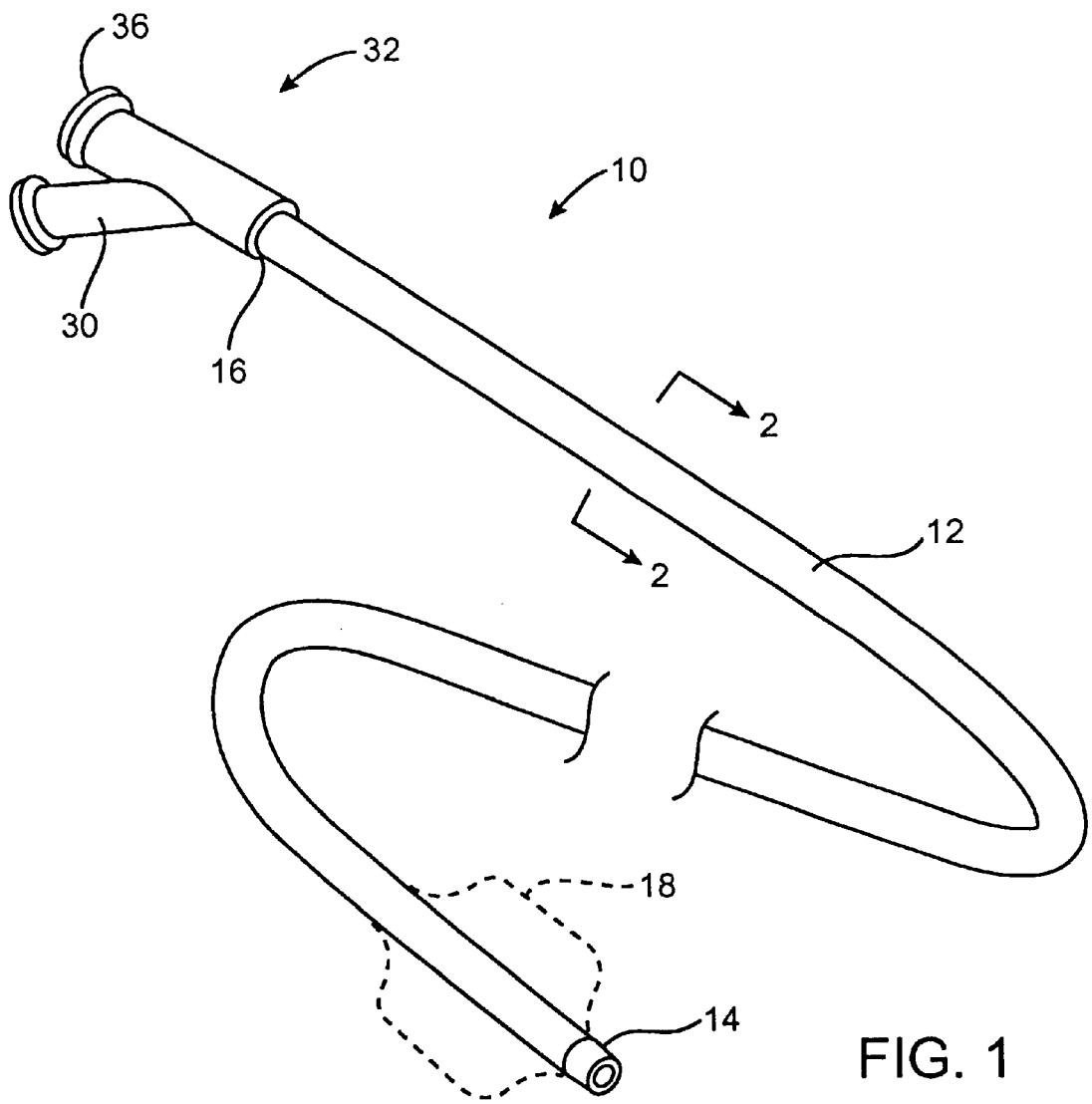
FIG. 1 is a perspective illustration of an access catheter useful in the methods, systems, and kits of the present invention.
Figure 2:
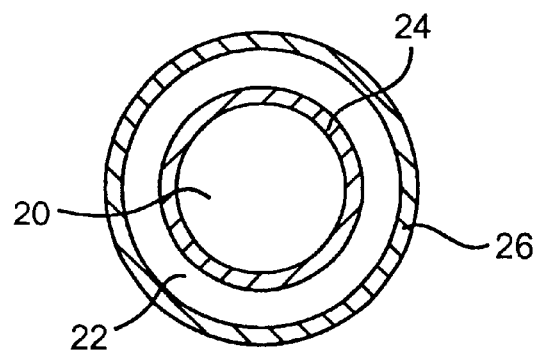
FIG. 2 is a cross-sectional view taken along line 2 to a FIG. 1.

The methods of the present invention will generally rely on accessing the target lung tissue segment using an access catheter adapted to be introduced endotracheally into the bronchus of the lung. An exemplary access catheter 10 is illustrated in FIGS. 1 and 2 and comprises a catheter body 12 having a distal end 14, a proximal end 16, and at least one lumen therethrough. Optionally, the catheter 10 further comprises an inflatable occlusion balloon 18 near its distal end. In this case, the catheter will have at least two lumens, a central lumen 20 and a balloon inflation lumen 22. As shown in FIG. 2, the balloon inflation lumen 22 may be an annular lumen defined by inner body member 24 and outer body member 26 which is coaxially disposed about the inner 5 body member. The lumen 22 opens to port 30 on a proximal hub 32 and provides for inflation of balloon 18. The central lumen 20 opens to port 36 on hub 32 and provides for multiple functions, including optional introduction over a guidewire, aspiration, introduction of secondary catheters, and the like.

Figure 4A:
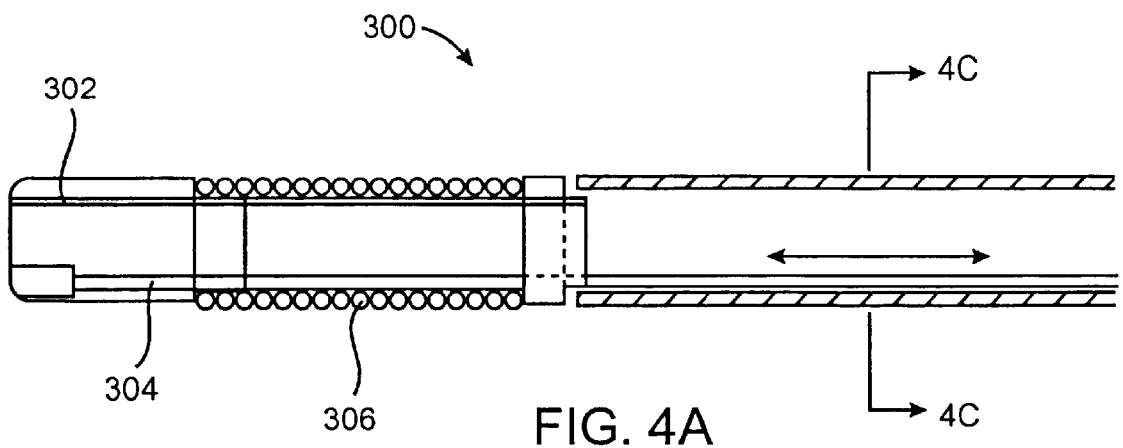
FIGS. 4A–4C illustrate a steerable imaging guidewire which may be used to facilitate positioning of the access catheter used in the methods of the present invention.
Figure 4B:
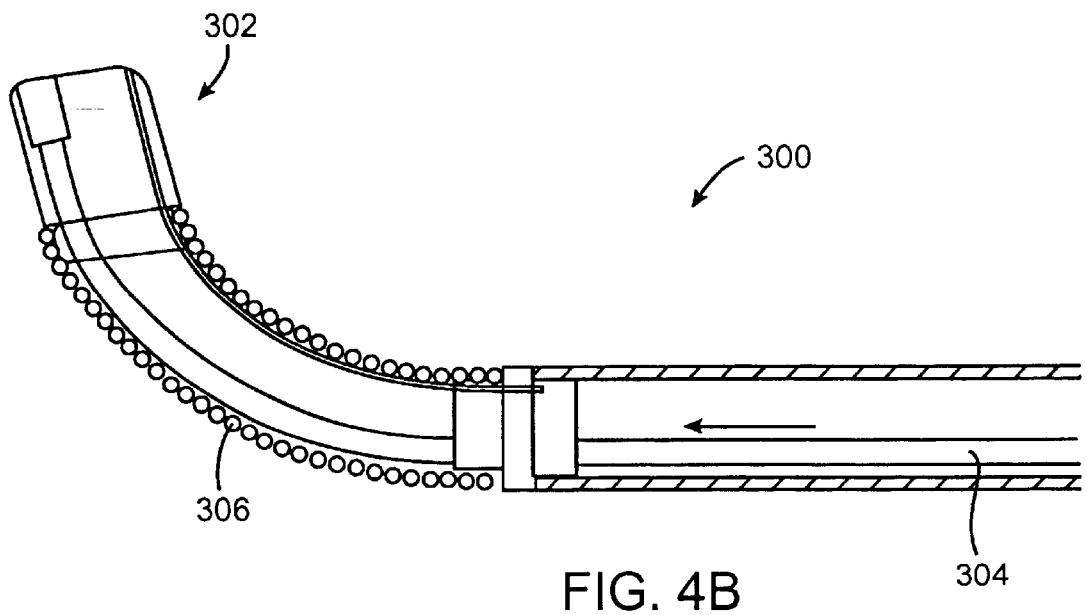

The dimensions and materials of access catheter 10 are selected to permit endotracheal introduction and intraluminal advancement through the lung bronchus or passageway, optionally over a guidewire and/or through a primary tracheal tube structure (as illustrated in FIG. 4B below). Suitable materials include low and high density polyethylenes, polyamides, nylons, PTFE, PEEK, and the like, particularly for the inner tubular member 24. The outer member, including the occlusion balloon, can be made from elastomeric materials, such as polyurethane, low density polyethylene, polyvinylchloride, silicone rubber, latex, and the like. Optionally, portions of the outer tubular member 26 proximal to the inflatable balloon can be made thicker and/or reinforced so that they do not dilate upon pressurization of the balloon. Exemplary dimensions for the access catheter 10 are set forth in the table below.

| ACCESS CATHETER DIMENSIONS | | | | |
|---|---|---|---|---|
| | Exemplary | | Preferred | |
| | Inner Tubular Member | Outer Tubular Member | Inner Tubular Member | Outer Tubular Member |
| Outer Dimension (mm) | 0.4–4 | 0.6–4.5 | 1–1.5 | 2–4 |
| Wall Thickness (mm) | 0.05–0.25 | 0.5–0.25 | 0.1–0.2 | 0.15–0.25 |
| Length (cm) | 50–150 | same | 50–80 | same |
| Balloon Length (mm) | 5–50 | | 10–20 | |
| Balloon Diameter (mm) (inflated) | 2–20 | | 6–15 | |

Figure 3A:
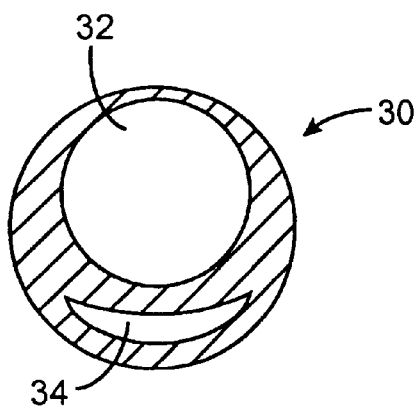
FIGS. 3A–3F illustrate alternative cross-sectional views of the access catheter of FIG. 1.
Figure 3B:
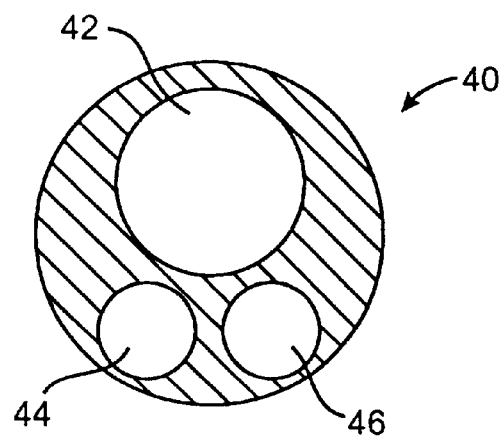
Figure 3C:
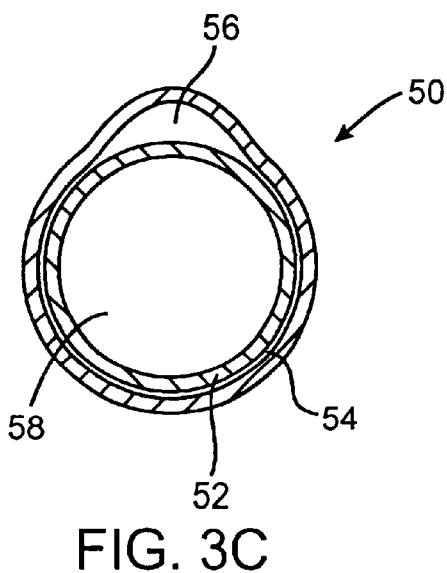
Figure 3D:
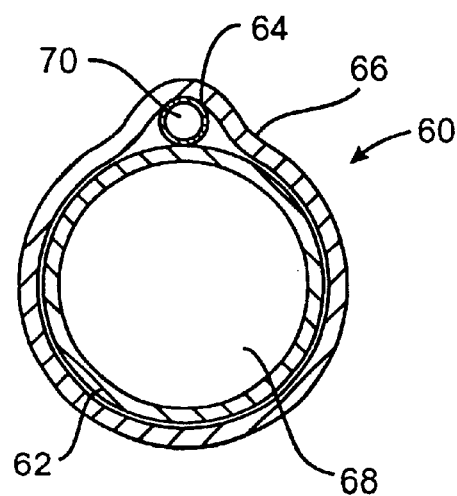

The access catheter 10 may be modified in a number of ways, some of which are illustrated in FIGS. 3A–3F. For example, instead of an inner and outer coaxial tube construction, the catheter can be a single extrusion having a catheter body 30 with a circular main lumen 32 and a crescent-shaped inflation lumen 34, as illustrated in FIG. 3A. Alternatively, catheter body 40 may be formed as a single extrusion having three lumens, i.e., a primary lumen 42 for receiving a guidewire, applying aspiration, and/or delivering secondary catheters. A second lumen 44 can be provided for inflating the occlusion balloon, and a third lumen 46 can be provided as an alternative guidewire or aspiration lumen. Catheter body 50 comprising a main tubular body 52 having an outer layer 54 fused thereover to define a lumen 56 suitable for balloon inflation as shown in FIG. 3C. A primary lumen 58 is formed within the main tubular member 52. As a slight alternative, catheter body 60 can be formed from a primary tubular member 62, and a secondary tubular member 64, where the tubular members are held together by an outer member 66, such as a layer which is applied by heat shrinking. The primary tubular member 62 provides the main lumen 68 while secondary tube 64 provides a secondary lumen 70. The secondary lumen 70 will typically be used for balloon inflation, while the primary lumen 68 can be used for all other functions of the access catheter.

Figure 3E:
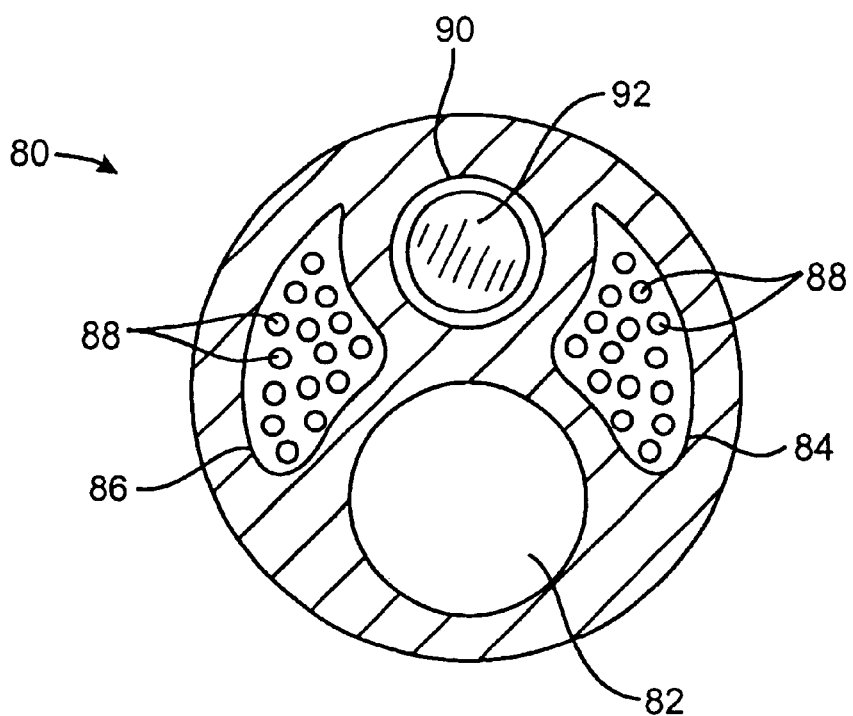
Figure 3F:
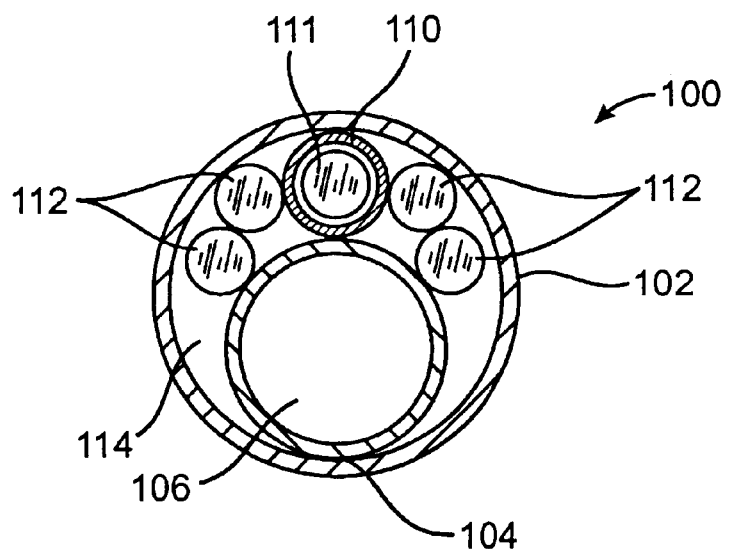

Optionally, the access catheter in the present invention can be provided with optical imaging capability. As shown in FIG. 3E, catheter body 80 can be formed to include four lumens, typically by conventional extrusion processes. Lumen 82 is suitable for passage over a guidewire. Lumens 84 and 86 both contain light fibers 88 for illumination. Lumen 90 carries an optical wave guide or image fiber 92. Lumen 82 can be used for irrigation and aspiration, typically after the guidewire is withdrawn. Balloon inflation can be effected through the space remaining and lumens 84 and 86 surrounding the light fibers 88. A second catheter body 100 is formed as a coaxial arrangement of a number separate tubes. Outer tube 102 contains a separate guidewire tube 104 defining lumen 106 which permits introduction over a guidewire as well as perfusion and aspiration after the guidewire is removed. Second inner tubular member 110 will carry an optical image fiber 112 and a plurality of light fibers 112 are passed within the remaining space 114 within the outer tubular member. In both catheter constructions 80 and 100, forward imaging can be effected by illuminating through the light fibers and detecting an image through a lens at the distal end of the catheter. The image can be displayed on conventional cathode-ray or other types of imaging screens. In particular, as described below, forward imaging permits a user to selectively place the guidewire for advancing the catheters through a desired route through the branching bronchus.

Figure 4C:
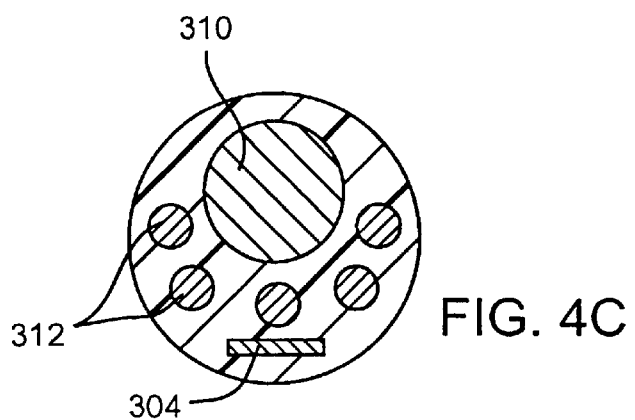

Usually, positioning of a guidewire through the branching bronchus will be manipulated while viewing through the imaging components of the access catheter. In this way, the access catheter can be "inched" along by alternately advancing the guidewire and the access catheter. As an alternative to providing the access catheter with imaging, positioning could be done solely by fluoroscopy. As a further alternative, a steerable, imaging guidewire 300 (FIGS. 4A–4C) could be used. The guidewire 300 includes a deflectable tip 302 which can be deflected in a single plane using push/pull ribbon 304. Usually, the tip will comprise a spring 306 to facilitate deflection. In addition to steerability, the guidewire 300 will include an optical imaging wave guide 310 and illuminating optical fibers 312, as best seen in cross-sectional view of FIG. 4C. Thus, the guidewire 300 can be steered through the branching bronchus to reach the target tissue segment using its own in situ imaging capability. Once the guidewire 300 is in place, an access catheter can be introduced to the target lung tissue segment as well. Since the guidewire has imaging capability, the access catheter need not incorporate such imaging. This can be an advantage since it permits the access lumen to be made larger since the catheter need not carry any optical wave guides.

Figure 5A:
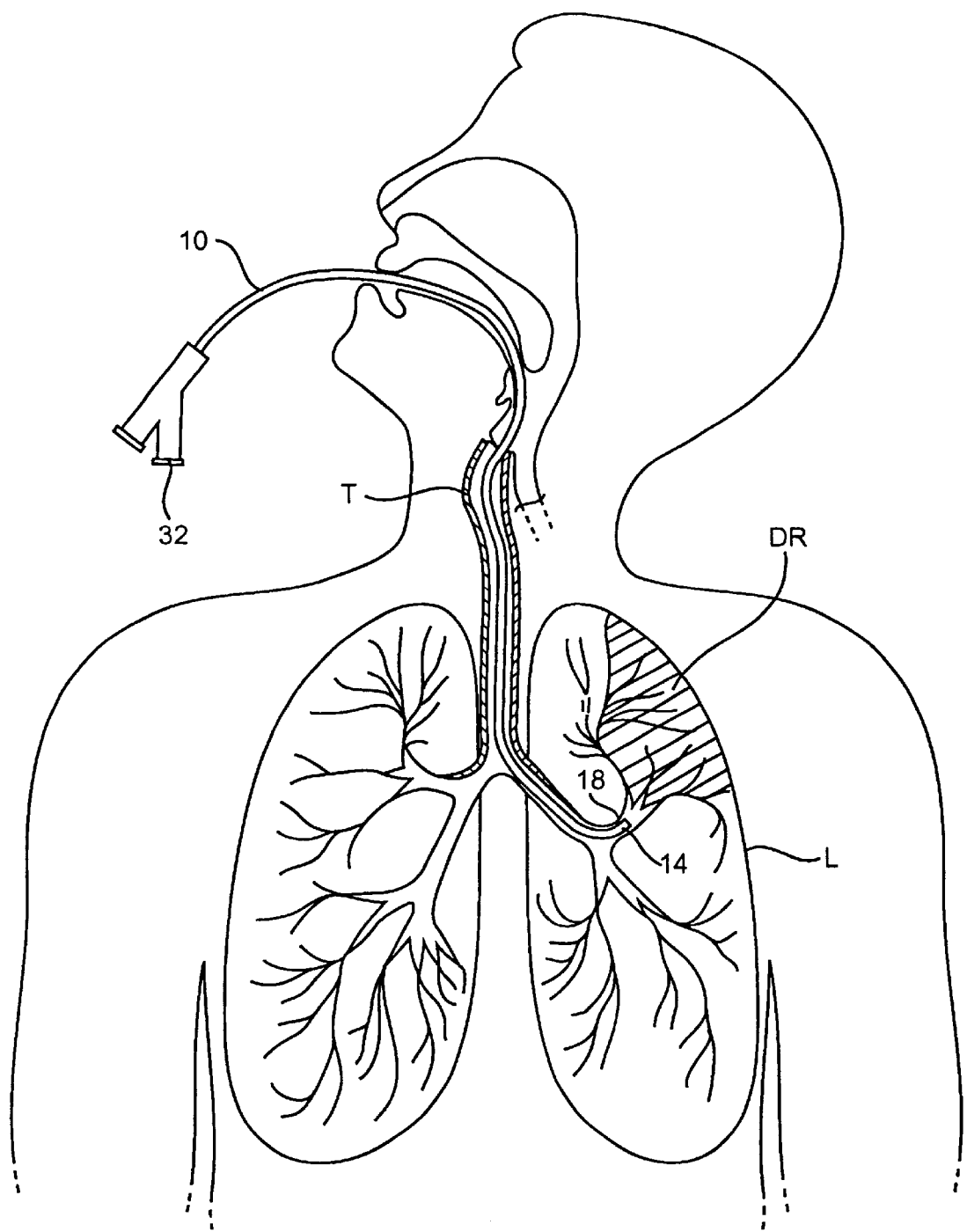
FIG. 5A illustrates use of the access catheter of FIG. 1 for accessing a target lung tissue segment according the to the methods of the present invention.
Figure 5B:
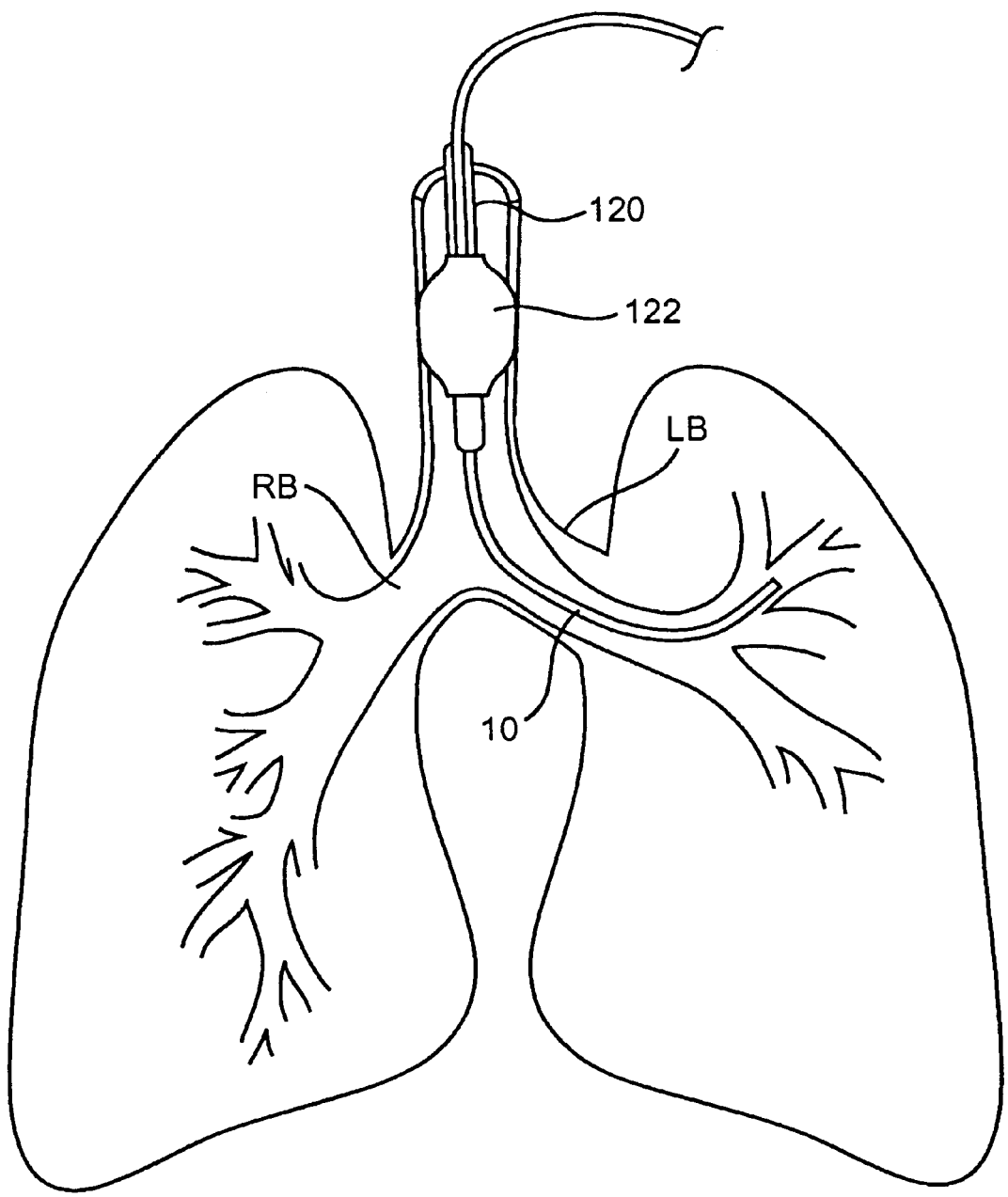
FIG. 5B illustrates use of a visualizing tracheal tube with the access catheter of FIG. 1 for accessing a target tissue segment according the to the methods of the present invention.

Referring now to FIG. 5A, a catheter 10 can be advanced to a lung tissue segment, specifically a diseased region DR, within a lung L through a patient's trachea T. Advancement through the trachea T is relatively simple and will optionally employ an endotracheal tube and/or a guidewire to select the advancement route through the branching bronchus. The endotracheal tube may have a thin-walled design wherein the inner diameter is larger than in standard endotracheal tubes. Standard endotracheal tubes have a 7.0 mm ID with a 10 mm OD. The thin-walled design would have a 9.0 mm ID with a 10 mm OD; the larger ID allows the insertion of a larger instrument while providing adequate ventilation. Steering can be effected under real time imaging using the imaging access catheters illustrated in FIGS. 3E and 3F. Optionally, the access catheter 10 may be introduced through a visualizing tracheal tube, such as that described in U.S. Pat. No. 5,285,778, licensed to the assignee of the present application. As shown in FIG. 5B, the visualizing endotracheal tube 120 includes an occlusion cuff 122 which may be inflated within the trachea just above the branch of the left bronchus and right bronchus LB and RB, respectively. The visualizing endotracheal tube 120 includes a forward-viewing optical system, typically including both illumination fibers and an image fiber to permit direct viewing of the main branch between the left bronchus LB and right bronchus RB. Thus, initial placement of the access catheter 10 can be made under visualization of the visualizing endotracheal tube 120 and optionally the access catheter 10 itself. It may be appreciated that the access catheter may be positioned with or without the use of a trachea tube or similar device. When such a device is used, it may take a number of forms and may be positioned in a number of locations. For example, the trachea tube or device may be positioned as shown in FIG. 5A, or it may be positioned to achieve "one lung ventilation" wherein the side of the lung not involved in the corrective procedure will be properly ventilated. Likewise, the access catheter may be positioned under local anesthesia without intubation. In any case, referring again in particular to FIG. 5A, the access catheter 10 is advanced until its distal end 14 reaches a region in the bronchus or lung passageway which leads directly into the diseased region DR.

Figure 6:
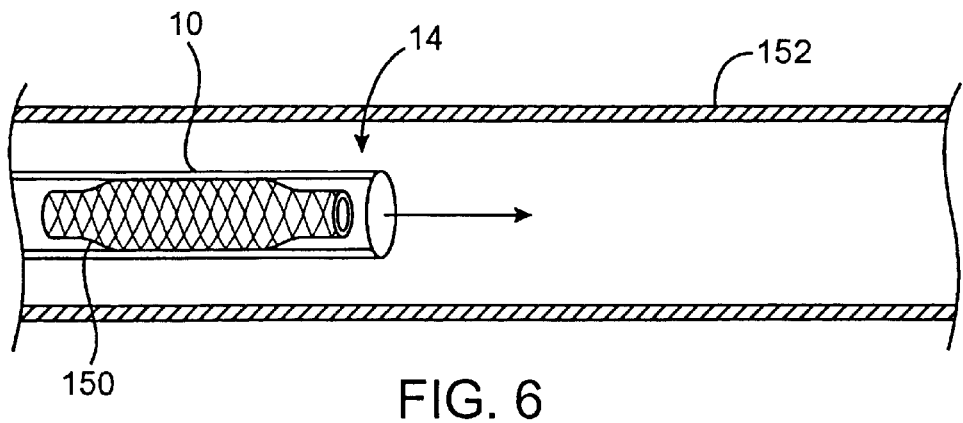
FIG. 6 illustrates a method of deployment or delivery of an obstructive device.

Once the distal end 14 of the access catheter 10 is positioned in a desired location within the lung passageway, an obstructive device may be deployed in the passageway. The method of deployment or delivery of the obstructive device is dependent on a number of factors, particularly the design of the obstructive device itself. Typically, the obstructive device is housed within the access catheter 10 or within a catheter that may be passed through the access catheter 10. As depicted in FIG. 6, the obstructive device 150 may be compressed or collapsed within an interior lumen of the access catheter 10. The obstructive device 150 depicted is one of many designs which may be utilized. The obstructive device 150 may then be pushed out of the distal end 14 of the catheter 10, in the direction of the arrow, into the lung passageway 152. If the device 150 is self-expanding, for example by tension or shape-memory, the device 150 will expand and anchor itself in the passageway 152. If the device 150 is not self-expanding, it may be expanded with the use of a balloon or other mechanism provided by the access catheter 10, a catheter or device delivered through the access catheter 10, or another device. Similarly, the obstructive device 150 may be mounted or crimped over the access catheter 10 (not shown) or a delivery catheter and delivered to the desired location. A sheath may then be placed over the device 150 during insertion. Deployment of the device 150 may be achieved by withdrawing the sheath and allowing the device 150 to self-expand or expanding the device 150 with the use of a balloon or other mechanism.

Figure 7A:
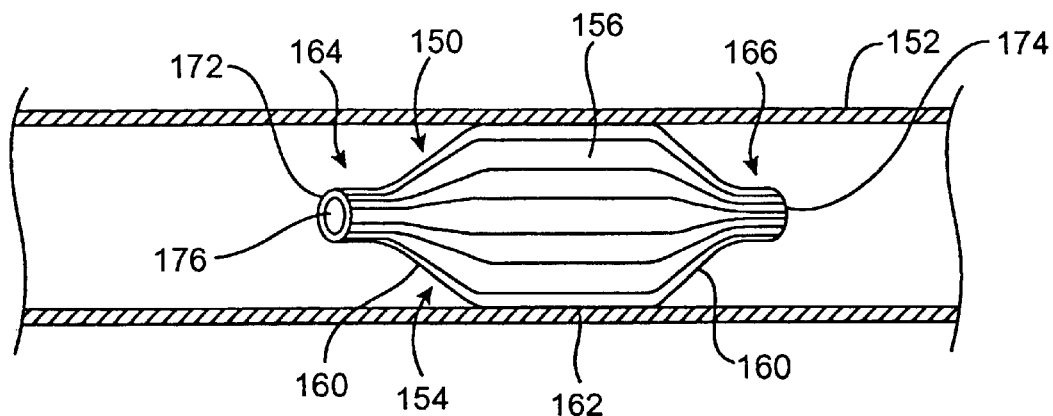
FIGS. 7A–7B are perspective views of embodiments of obstructive devices having, among other features, radial and longitudinal structural supports.
Figure 7B:
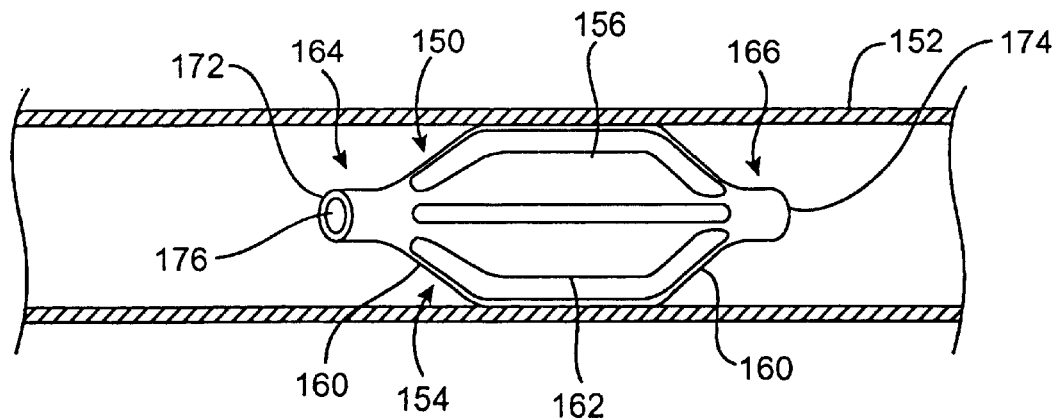

A variety of embodiments of obstructive devices 150 are provided. To begin, a number of embodiments of the obstructive device 150 are comprised of structural supports which expand to anchor the device 150 in the passageway 152. Referring to FIG. 7A, the supports 154 may be comprised of radial segments 160 and longitudinal segments 162. The radial segments 160 allow the device 150 to expand to fill the passageway 152 and the longitudinal segments 162 rest against the walls of the passageway 152 to help anchor the device 150. The supports 154 may be individual, as shown in FIG. 7A, or may be connected to one another, as shown in FIG. 7B, for example. In addition, the supports 154 may continue along a proximal end 164 and distal end 166 of the device 150, as shown in FIG. 7A, or the supports 154 may not be present at such ends 164, 166, as shown in FIG. 7B.

Figure 8:
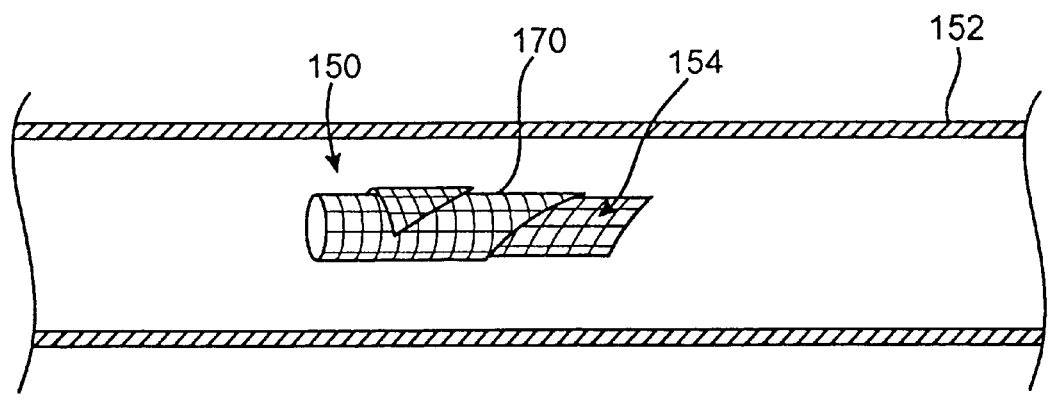
FIG. 8 is a perspective view of an embodiment of an obstructive device in a rolled configuration prior to release in a lung passageway.
Figure 9:
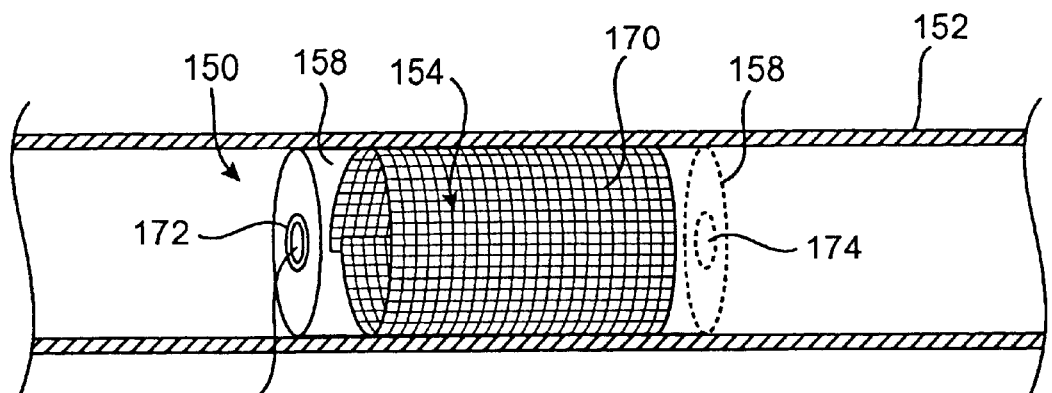
FIG. 9 is a perspective view of an embodiment of a rolled, cylindrical shaped obstructive device in an expanded state within a flexible sack.
Figure 10:
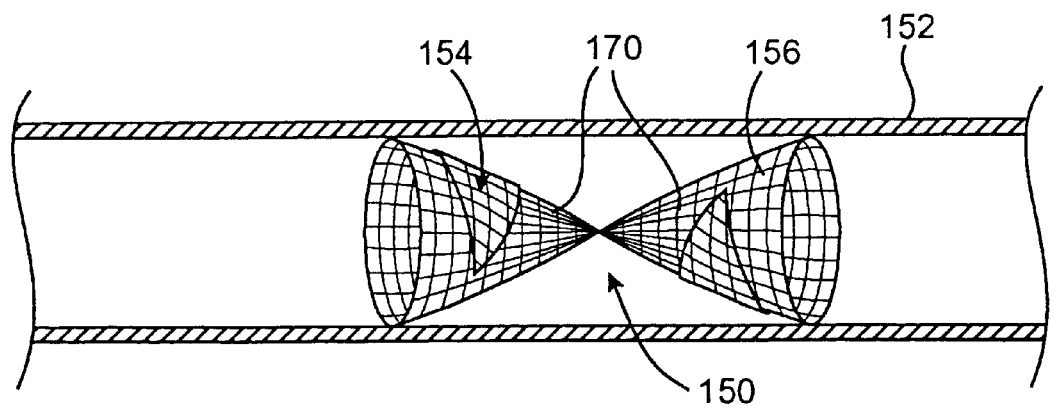
FIG. 10 illustrates an embodiment of a double conical shaped obstructive device.
Figure 11:
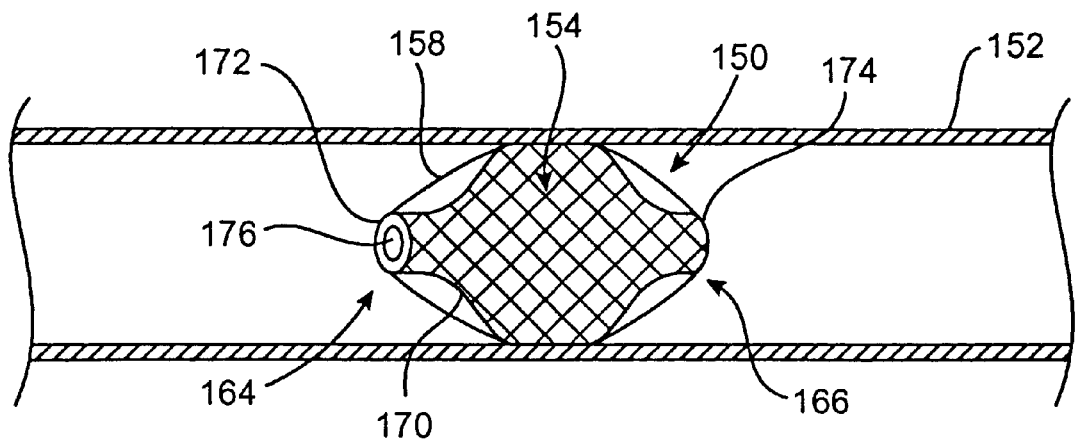
FIG. 11 is a perspective view of an embodiment of an obstructive device having, among other features, a mesh structural support encased by a polymer film.

Referring to FIGS. 8–11, the supports 154 may be comprised of a mesh 170 or similar interlocking structure. As shown in FIG. 8, the mesh 170 may be coiled or rolled into a cylindrical shape to fit within an inner lumen of a delivery or access catheter or to be mounted on the end of a such a delivery or access catheter. In either case, the device 150 may be released within the lung passageway 152 where the mesh 170 expands, uncoils and/or unrolls to fill the passageway 152. Such release may allow self-expansion or may involve the use of mechanical means to expand the mesh 170. The expanded device 150 may fill the passageway 152 in a generally cylindrical shape, as shown in FIG. 9, in single or double conical shape, as shown in FIG. 10, or it may form a variety of other shapes, an example of which is shown in FIG. 11.

Figure 12:
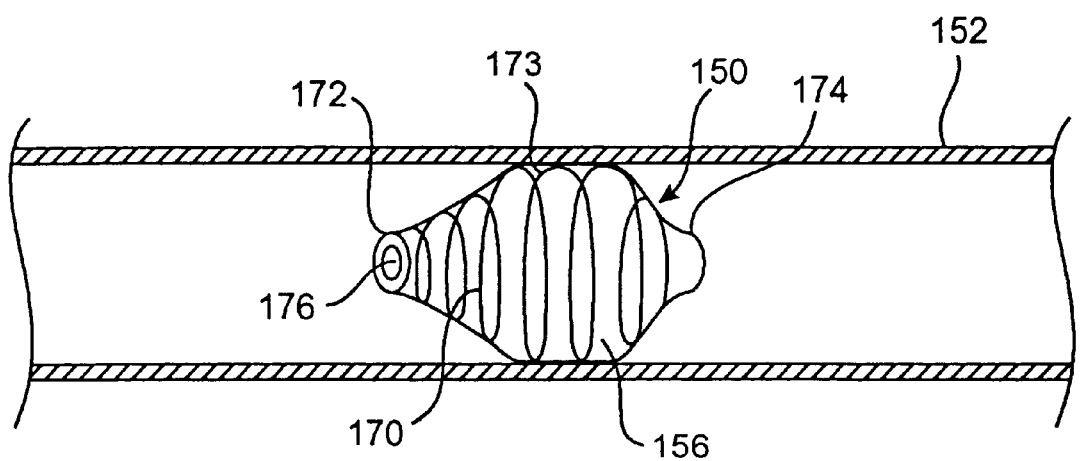
FIG. 12 is a perspective view of an embodiment of an obstructive device having, among other features, a spiral structural support.

Referring now to FIG. 12, the supports 154 may be a helix or spiral 171 comprised of helically wound or spiral wound wire. The spiral 171 may be compressed in a number of ways to load the spiral 171 within a lumen or on a distal end of a delivery catheter. For example, the spiral 171 may be wound tightly, similar to a watch spring, to reduce the cross-section of the spiral and provide spring tension. Upon release of the spiral 171, the coils 173 expand to contact the walls of the passageway 152 and anchor the device 150.

In any of the above embodiments, the supports 154 may be connected to, encapsulated in, coated or impregnated with a material to prevent flow of gases or liquids through the structural supports 154, thereby providing an obstruction. In addition, the material may include an antibiotic agent for release into the lung passageway. Examples of obstructive materials include a thin polymer film 156, such as webbing between the structural supports 154, which may be used to seal against the surface of the lung passageway 152. Such a design is depicted in FIGS. 7A–7B, 10 and 12. Similarly, the structural supports 154 may be filled with an adhesive or sealant which will adhere the structural support members together and prevent flow or gasses or liquids through the device 150. This is particularly useful in coiled or mesh designs in where the structural support members are relatively close together. Alternatively, as shown in FIG. 9 and FIG. 11, the supports 154 may be encased in a sack 158 comprised of a thin polymer, foam or other material. Expansion of the supports 154 within the sack 158 presses the sack 158 against the walls of the passageway 152 forming a seal. In FIG. 9, the sack 158 has been extended beyond the ends of the rolled support structure 154 for illustration purposes to differentiate between the sack 158 and support structure 154. However, typically, the support structure 154 will fill the sack 158. Again, the presence of the sack 158 prevents flow of gases or liquids through the supports 154, thereby providing an obstruction. It may be appreciated that the structural supports may comprise a variety of designs, creating devices 150 of various lengths and shapes. Alternatively, the sack 158 may be utilized without structural supports 154. The sack may expand to fill the passageway by a variety of methods and may be held in position by impregnation with an adhesive or other material. Such impregnation may rigidify or support the sack to provide obstruction of the lung passageway.

Figure 13:
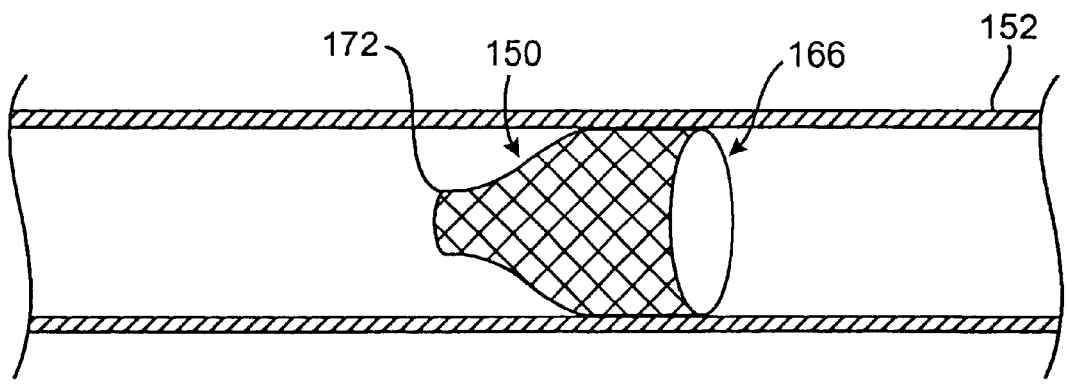
FIG. 13 is a perspective view of an embodiment of an obstructive device having a cone shape with an inlet port at the apex of the cone.

In addition and also shown in FIGS. 7A, 7B, 9, 11–13, a number of embodiments of the obstructive device 150 include an inlet port 172, located near the proximal end 164, and an outlet port 174, located near the distal end 166. Such ports 172, 174 may be of any size or shape but are typically round or oval and are often located near the center of the passageway 512 lumen for ease of accessibility. Some devices 150 may only include an inlet port 172 near the proximal end 164, as shown in FIG. 13. In this case, the distal end 166 is expanded to contact the walls of the lung passageway 152 and anchor the device 150. Thus, the obstruction device 150 appears to have a cone shape with the inlet port 172 at the apex of the cone. To ensure concentric placement of the obstruction device 150, the device 150 should contact the walls of the passageway 152 for a length of at least 1.0 to 1.5 times the internal diameter of the passageway that the device 150 occupies.

Figures 14A, 14B, 14C:
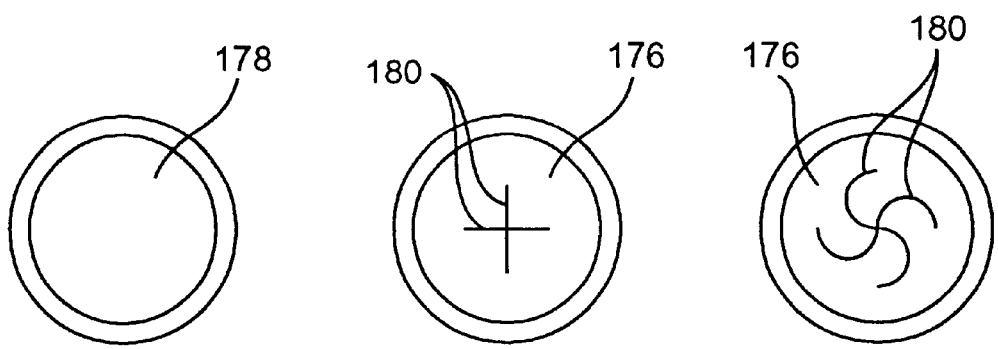
FIGS. 14A–14C illustrate embodiments of self-sealing septums of the present invention.

The inlet port 172, outlet port 174 or both may comprise a membrane or septum 176 covering the opening of the port. The septum 176 will typically be self-sealing. One type of self-sealing septum 176 comprises a solid membrane 178, illustrated in FIG. 14A. Other types comprise pre-cut membranes in which the septum 176 includes cuts 180 or slits, as shown in FIGS. 14B and 14C. Such cuts 180 may allow ease of penetration through the septum 176 by an access tube or penetrating element, as will be later described, while preventing flow through the septum when the penetrating element is removed.

Figure 15:
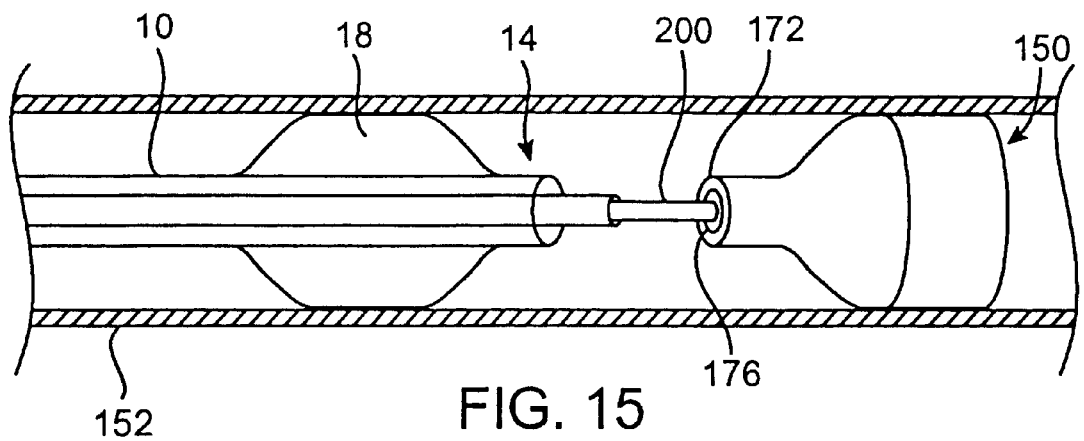
FIG. 15 illustrates a method of aspirating through an obstructive device by inserting an access tube through a septum of an inlet port.

After the obstruction device 150 is deployed and anchored within a lung passageway 152 leading to a lung tissue segment, the device 150 may be left as an implant to obstruct the passageway 152 from subsequent airflow. Airflow may include air and/or any other gas or combination of gases, such as carbon dioxide. However, immediately after placement or at any time thereafter, the above described embodiments of the device 150 may be accessed to aspirate the lung tissue segment through the obstructive device 150. This will cause the segment to at least partially collapse as part of a method for lung volume reduction. Aspirating through the obstructive device 150 may be accomplished by a variety of methods. For example, referring to FIG. 15, aspiration may be achieved by first inserting a penetration element, needle or access tube 200 through the septum 176 of the inlet port 172. Positioning of the access tube 200 for such insertion may be achieved by any method, however, the access tube 200 is typically positioned by inserting the access tube 200, or a catheter carrying the access tube 200, through a lumen in the access catheter 10 until it passes out of the distal end 14. Inflating the balloon 18 on the access catheter 10 may center the distal end 14 of the catheter in the lung passageway 152. If the inlet port 172 is similarly centered, the access tube 200 may be passed directly out of the catheter 10 and through the septum 176 of the inlet port 172.

If the septum 176 is a solid membrane 178, the access tube 200 may be sharp enough to puncture or pierce the membrane 178. If the septum 176 has cuts 180 or slits, the access tube 200 may be pushed through the cuts 180. In either case, the membrane or septum 176 will seal around the access tube 200. If the obstruction device 150 also has an outlet port 174, the access tube 200 may optionally be passed through both the inlet and outlet ports 172, 174. Once the access tube 200 is inserted, gases and/or liquids may be aspirated through the access tube 200 from the lung tissue segment and associated lung passageways. Optionally, prior to aspiration, a 100% oxygen, Helium-Oxygen mixture or low molecular weight gas washout of the lung segment may be performed by introducing such gas through the access tube 200. In this case, aspiration would removed both the introduced gas and any remaining gas. Similarly, liquid perfluorocarbon or certain drugs, such as antibiotics, may be introduced prior to aspiration. This may allow access to the collapsed lung segment at a later time, for example, in the case of an infection. In most cases, aspiration will at least partially collapse the lung segment, as previously described. The access tube 200 may then be withdrawn. The septum 176 of the inlet port 172 and/or outlet port 174 will then automatically seal, either by closing of the puncture site or by closure of the cuts. Optionally, the ports may be additionally sealed with a sealant or by use of a heat source or radiofrequency source.

Figure 16:
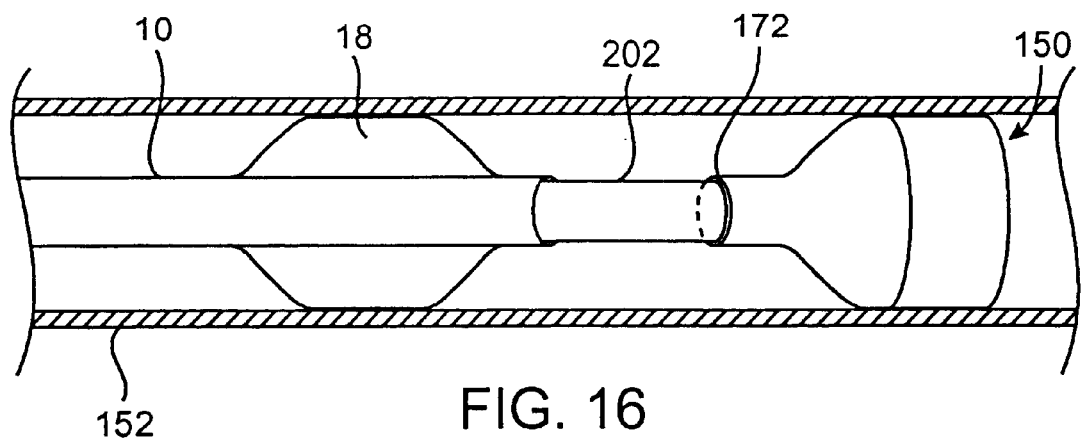
FIG. 16 illustrates a method of aspirating through an obstructive device by contacting an aspiration catheter to an inlet port.
Figure 17:
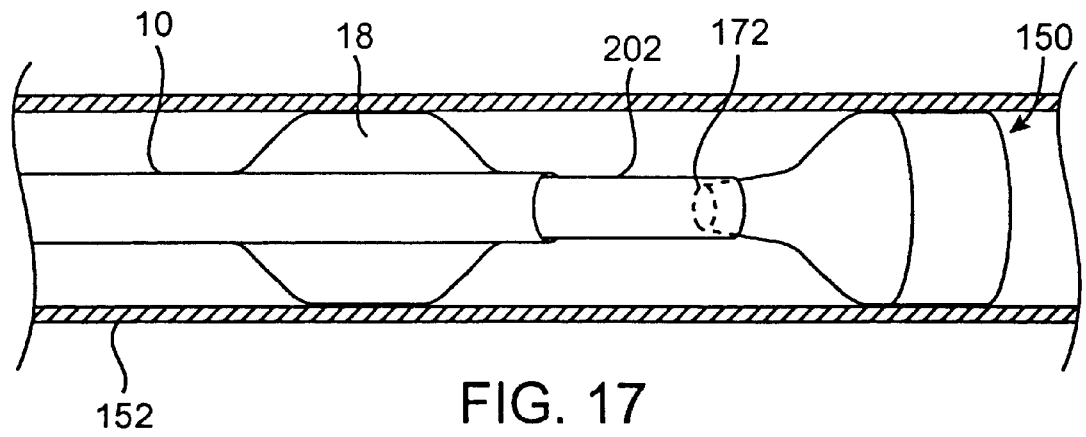
FIG. 17 illustrates a method of aspirating through an obstructive device by sliding the distal end of an aspiration catheter over an inlet port.

Referring to FIGS. 16 and 17, aspiration through the obstructive device 150 may be achieved by contacting the obstructive device 150 with a suction tube or aspiration catheter 202 and aspirating gas or liquids through the device 150. As shown in FIG. 16, the distal end 204 of the aspiration catheter 202 may be held against the inlet port 172. Positioning of the aspiration catheter 202 for such contact may be achieved by any method, however the catheter 202 is typically positioned in a manner similar to the access tube described above. By holding the aspiration catheter 202 against the port 172, a seal may be created and gases and/or liquids may be aspirated from the lung tissue segment through the device 150. In this case, the inlet port 172 and the outlet port 174, if present, must not be covered by a solid membrane 178. If cuts 180 are present, the gas or liquid may flow through the port due to the pressure of the suction. As shown in FIG. 17, the distal end 204 of the aspiration catheter 202 may be slid over the inlet port 172 to form a seal. Again, gases and/or liquids may then be aspirated through the device 150 in a similar manner. The aspiration catheter 202 may then be withdrawn. The septum 176 of the inlet port 172 and/or outlet port 174 will then automatically seal, typically by closure of the cuts. Optionally, the ports may be additionally sealed with a sealant or by use of a heat source or radiofrequency source.

Figure 18A:
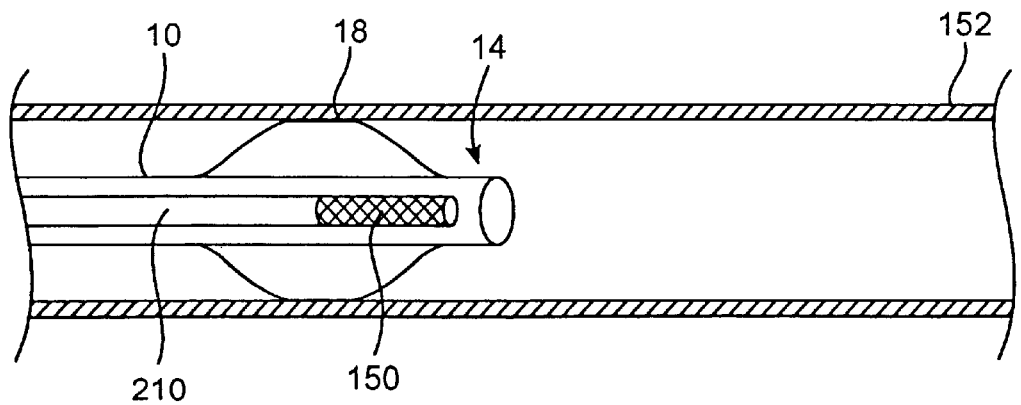
FIGS. 18A–18C illustrate a method of deploying, anchoring and aspirating through an obstruction device while such a device is connected to an aspiration catheter.
Figure 18B:
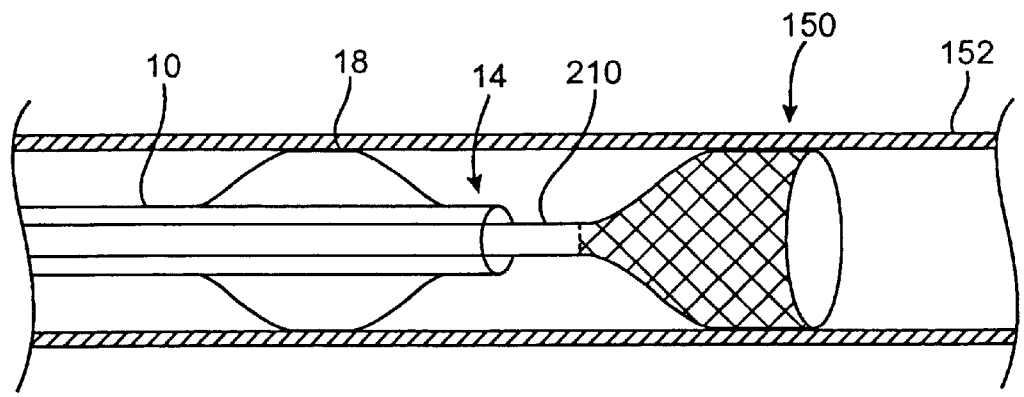
Figure 18C:
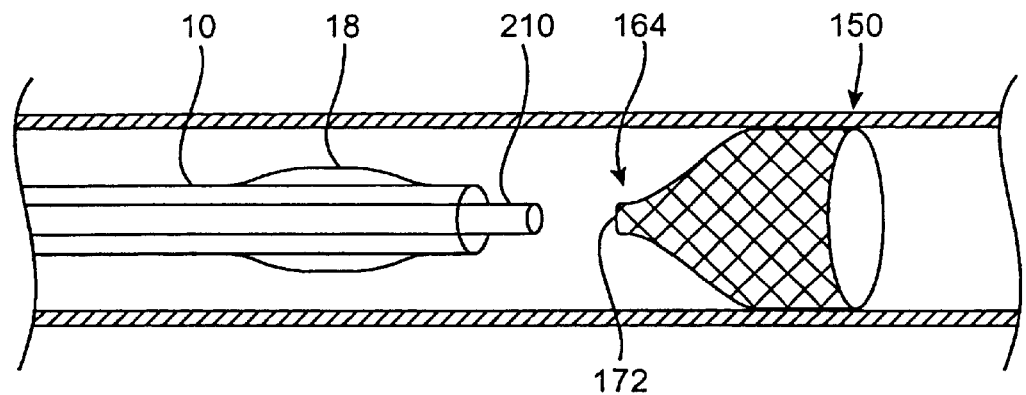

Referring to FIGS. 18A–18C, the obstruction device 150 may be deployed, anchored and aspirated therethrough while connected to an aspiration catheter 210. In this case, the access catheter 10 is positioned within the lung passageway 152 at a desired location. If the catheter 10 has an inflatable occlusion balloon 18 near its distal end 14, the balloon 18 may be inflated to secure and center the catheter 10 within the passageway 152; however, this step is optional. As shown in FIG. 18A, an aspiration catheter 210 carrying an obstruction device 150 is then introduced through a lumen in the access catheter 10. As shown in FIG. 18B, the aspiration catheter 210 is advanced so that the obstruction device 150 emerges from the distal end 14 of the access catheter 10 and deploys within the lung passageway 152. Expansion and anchoring of the obstruction device 150 within the passageway 152 may be achieved by self-expansion or by expansion with the aid of a balloon, for example. The lung tissue segment isolated by the device 150 is then aspirated through the device 150 and the attached aspiration catheter 210. Such aspiration may remove air, gases, or liquids from the segment and lung passageway 152 to at least partially collapse the lung segment. As shown in FIG. 15C, the obstruction device 150 is then detached from the aspiration catheter 210 and left behind in the passageway 152. The proximal end 164 of the obstruction device 150 may comprise an inlet port 172 which would allow subsequent access to the isolated lung tissue segment at a later time. Alternatively, the proximal end 164 may comprise a sealed end, wherein the obstruction device 150 may not be subsequently accessed and may provide long-term isolation of the terminal lung tissue segment.

It may be appreciated that the above described method may be similarly achieved without the use of an aspiration catheter 210. In this case, the obstruction device 150 may be carried directly by the access catheter 10 and may be deployed while remaining attached to the access catheter 10. Aspiration may be achieved through the obstruction device 150 and the access catheter 10 to remove gases from the isolated lung tissue segment and passageway 152. The obstructive device 150 may then be detached from the access catheter 10 and left behind in the passageway 152 for subsequent access or simple occlusion.

At this point, all catheters and instruments may be withdrawn from the patient and the obstruction device 150 may remain in its anchored position, as described. The obstruction device 150 will essentially occlude the lung passageway 152 and prevent the inflow or outflow of air or gases to the isolated lung tissue segment or diseased region DR. This may be effective in maintaining the desired level of collapse of the lung tissue segment to achieve lung volume reduction. However, at any point, the lung tissue segment may be reaccessed and/or reaspirated by repeating the steps described above. In addition, at any point, the obstruction device 150 may be removed from the lung passageway 152, either by collapse of the expandable structure or by other means.

Additional embodiments of the obstructive device 150 are comprised of a unidirectional valve. The valve may be operated upon access or it may operate in response to respiration. For example, when the valve is positioned in the lung passageway, the valve may be accessed by engaging an aspiration catheter or a coupling member to the valve. Aspiration through the aspiration catheter or coupling member then opens the valve to remove gases and/or liquids from the isolated lung segment. Alternatively, the valve may open automatically in response to respiration. The valve may open during expiration to allow outflow of gas from the lung segment and the close during inspiration to prevent inflow of gas to the lung segment. In either case, the unidirectional valves may take a number of forms.

Figure 19A:
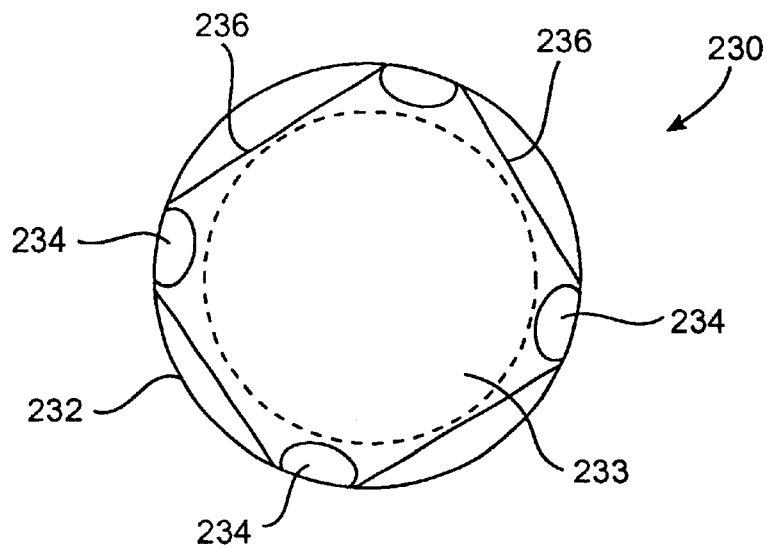
FIG. 19A is a front view of an embodiment of a unidirectional valve of the present invention.
Figure 19B:
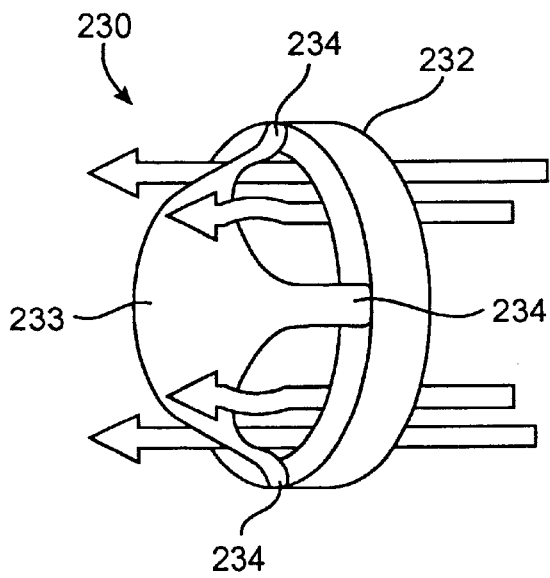
FIGS. 19B–19C are perspective views of the unidirectional valve of FIG. 19A in various stages of operation.
Figure 19C:
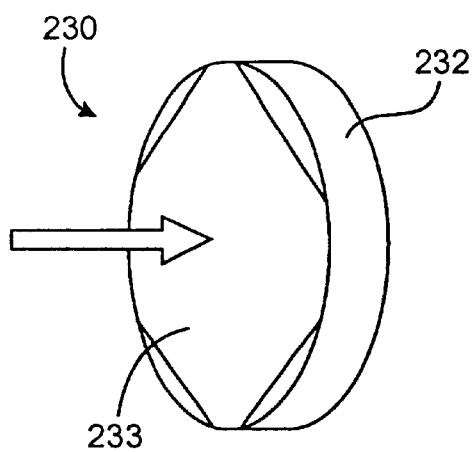

One embodiment of such a unidirectional valve is illustrated in FIGS. 19A–19C. In this embodiment, the unidirectional valve 230, front-view shown in FIG. 19A, is comprised of a port 232 and a flexible layer 233 which is attached to the port 232 by at least one point of connection 234. As shown, the flexible layer 233 may be attached to the front surface of the port 232 at four symmetrical points of connection 234. In preferred embodiments, edges 236 of the layer 233 are positioned outside of the opening of the port 232 (indicated by dashed lines). This provides a desired seal when the valve is in the closed position.

Side-views shown in FIGS. 19B and 19C depict the valve 230 during different stages of the respiratory cycle. During expiration, the valve 230 opens, as depicted in FIG. 19B. Here, expiration of gases is illustrated by arrows. Gases exiting through the lung passageway, within which the valve 230 is positioned, apply force to the backside of the flexible layer 233 causing the layer 233 to expand outwardly away from the surface of the port 232 as shown. This allows the gases to flow through the spaces between the points of connection 234. During inspiration, the valve 230 closes, as depicted in FIG. 19C. Here, inspiration of air is illustrated by an arrow. Air entering the lung passageway applies force to the front side of the flexible layer 233 causing the layer 233 to seal against the surface of the port 232 as shown. This prevents gases from flowing through the valve 230.

Figure 20:
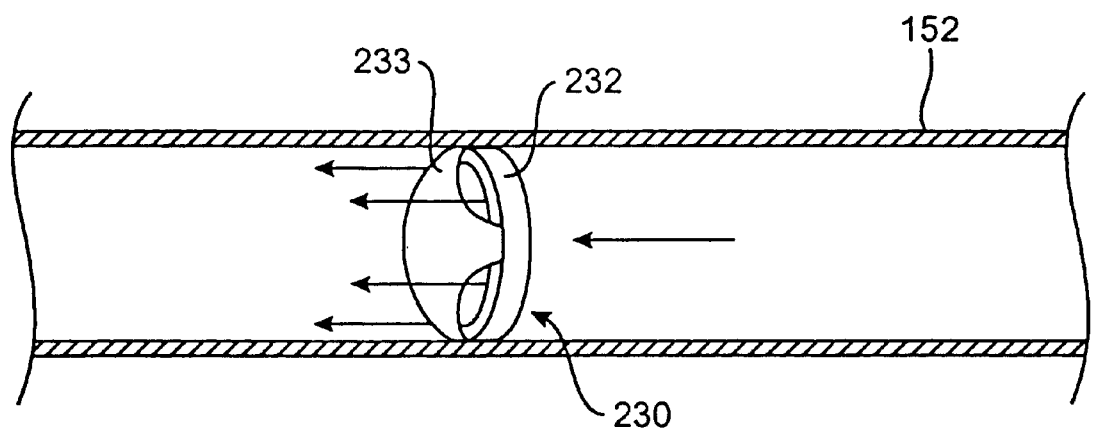
FIGS. 20–21 illustrate positioning of embodiments of unidirectional valves of the present invention in a lung passageway.
Figure 21:
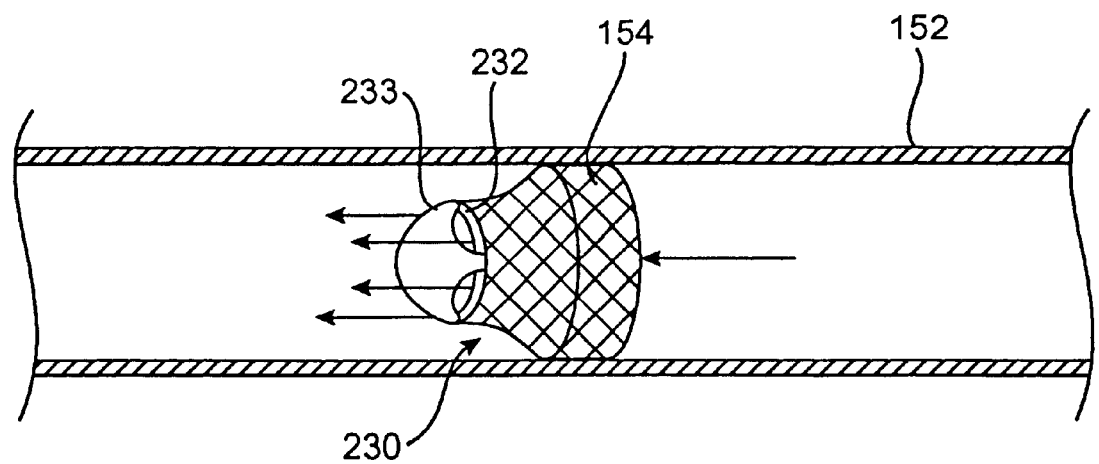

Unidirectional valves 230 may be positioned in the lung passageway 152 by methods similar to those previously described for other types of obstruction devices 150. As shown in FIG. 20, the valve 230 may be positioned in the passageway 152 so that the outside perimeter of the port 232 contacts the walls of the passageway 152. In this way, the valve 230 is essentially the size of the passageway lumen and provides the maximum area for potential flow-through of gas. The valve 230 is depicted in its open state, with gas flow traveling from an isolated lung tissue segment, through the valve and out of the patient's airways. As shown in FIG. 21, the valve 230 may alternatively be attached to or part of structural supports 154 which expand radially to anchor the device 150 in the passageway 152. Such supports 154 are similar to those previously described. Again, the valve 230 is depicted in its open state. It may be appreciated that the valve 230 may be of any size or shape and may substituted for any of the inlet and/or outlet ports previously described.

Figure 22A:
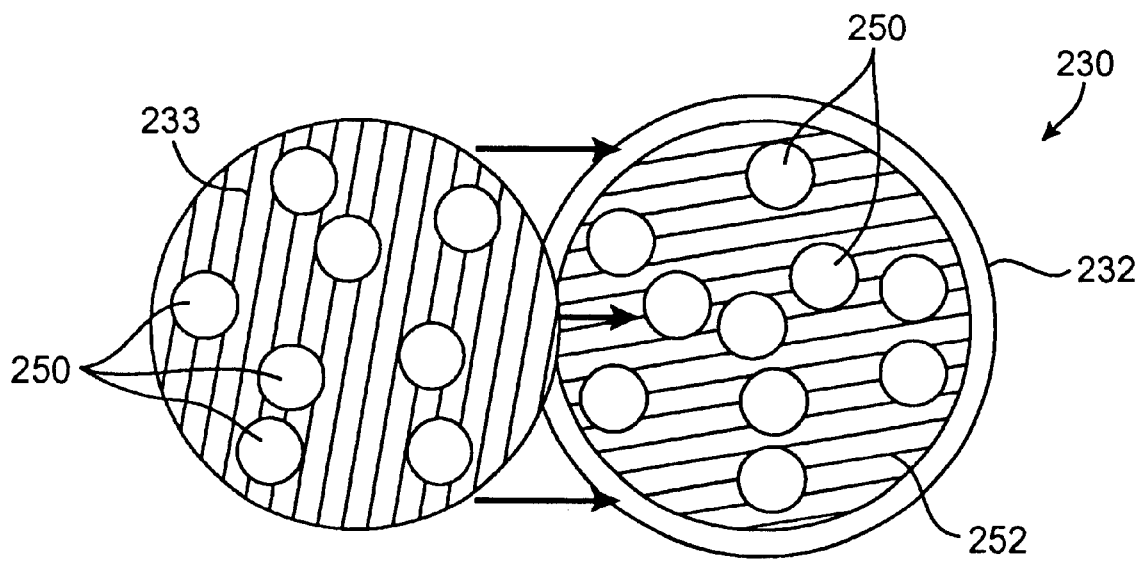
FIGS. 22A–22B are front views of an embodiment of a unidirectional valve of the present invention.
Figure 22B:
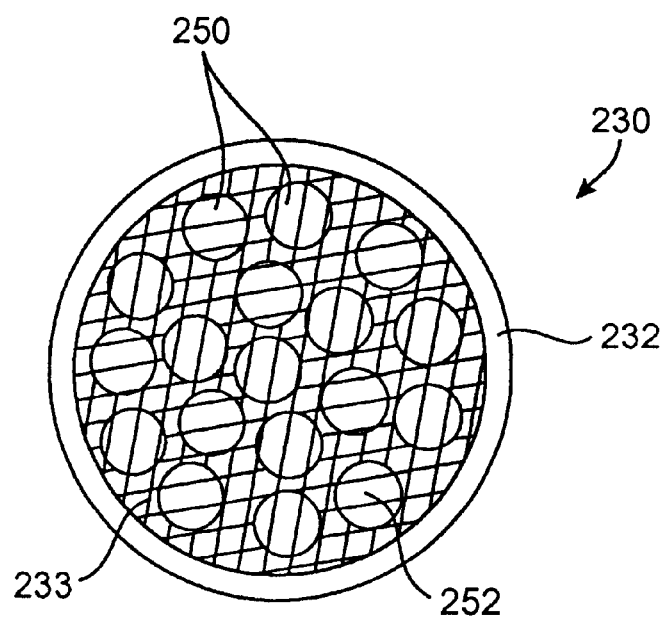

Another embodiment of a unidirectional valve is illustrated in FIGS. 22A–22B. In this embodiment, the valve 230 is comprised of a port 232 and a flexible layer 233 as in the previous embodiment. However, here the flexible layer 233 has a series of holes 250 through the layer. In addition, the valve 230 is comprised of a partition 252 which also has holes 250. The holes 250 may be of any size, shape or arrangement throughout the entire or a portion of the layer 233 and partition 252. The partition 252 covers the port 232 and the layer 233 is positioned over the partition 252, as illustrated in FIG. 22A and depicted by arrows, so that the holes 250 are substantially misaligned and therefore blocked. The assembled valve, illustrated in FIG. 22B, does not have any through holes 250 in the closed position. The holes 250 in the layer 233 are blocked by the underlying partition 252. Likewise, the holes 250 in the partition 252 are blocked by the overlying layer 233. The layer 233 is attached to the partition 252 and/or port 232 along its perimeter; it may be a continuous attachment or may have discrete points of connection with spaces therebetween.

Figure 23A:
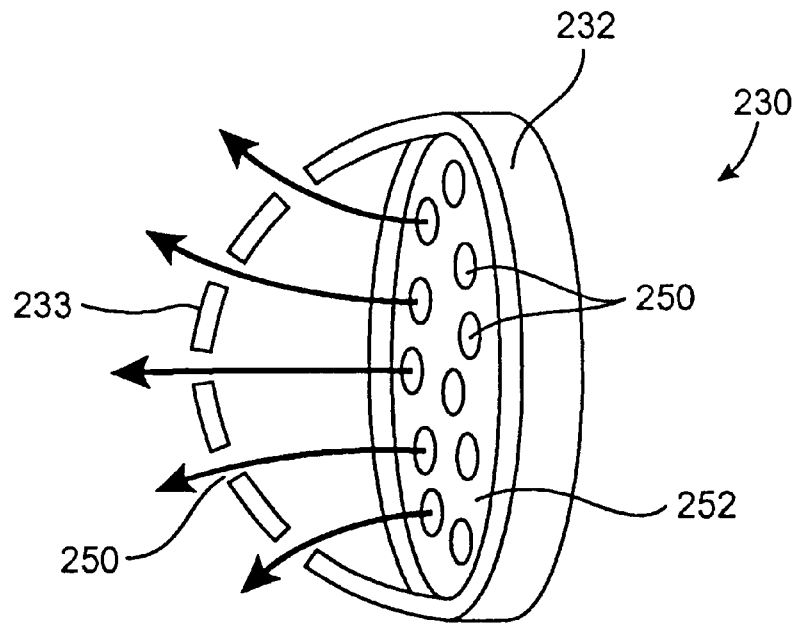
FIGS. 23A–23B are perspective views of the unidirectional valve of FIGS. 21A–21B in various stages of operation.
Figure 23B:
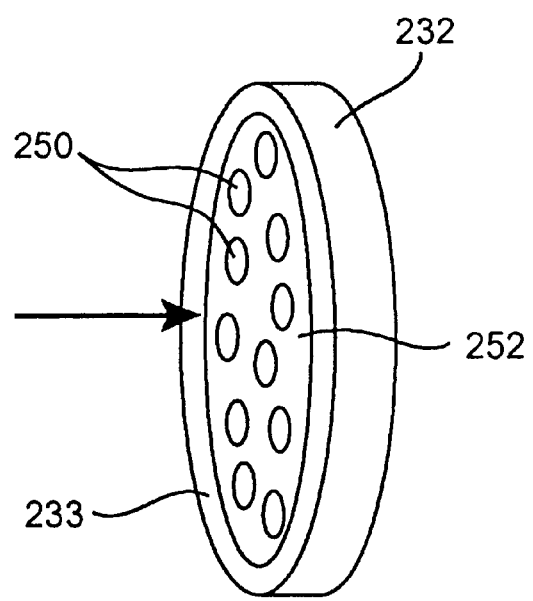

Side-views shown in FIGS. 23B and 23C depict the valve 230 during different stages of the respiratory cycle. During expiration, the valve 230 opens, as depicted in FIG. 23B. Here, expiration of gases is illustrated by arrows. Gases exiting through the lung passageway, within which the valve 230 is positioned, pass through the holes 250 in the partition 252 and apply force to the backside of the flexible layer 233. This causes the layer 233 to expand outwardly away from the partition 252 as shown. This allows the gases to flow through the holes 250 in the layer 233. During inspiration, the valve 230 closes, as depicted in FIG. 23C. Here, inspiration of air is illustrated by an arrow. Air entering the lung passageway applies force to the front side of the flexible layer 233 causing the layer 233 to seal against the surface of the partition 252 as shown. This prevents gases from flowing through the valve 230. This embodiment of a unidirectional valve 230 may be positioned in a lung passageway 152 by methods similar to those previously described for other types of obstruction devices 150, particularly as shown in FIGS. 20 and 21.

Although the unidirectional valves described above are shown as operating during different stages of the respiratory cycle, the valves may additionally or alternatively be operated manually. Valves positioned in a lung passageway, as depicted in FIGS. 20–21, may be accessed by coupling an aspiration catheter to the valve. Coupling may comprise engaging the aspiration catheter, a suitable catheter or a coupling member to the valve. In some cases, particularly when the valve 230 comprises a port 232 which is smaller in diameter than the lumen of the lung passageway, as depicted in FIG. 21, the distal end of the aspiration catheter or coupling member may be slid over the port to form a seal. This was previously depicted in FIG. 17 in relation to sealing of the aspiration catheter 202 around an inlet port 172 of a non-valved obstruction device. When a valve is present in this case, aspiration through the aspiration catheter will open the valve and draw gases and/or liquids from the lung tissue segment. With the described unidirectional valves 230, the suction force of the aspiration will draw the flexible layer 233 away from the port 232 or the partition 252 to open the valve.

Figure 24:
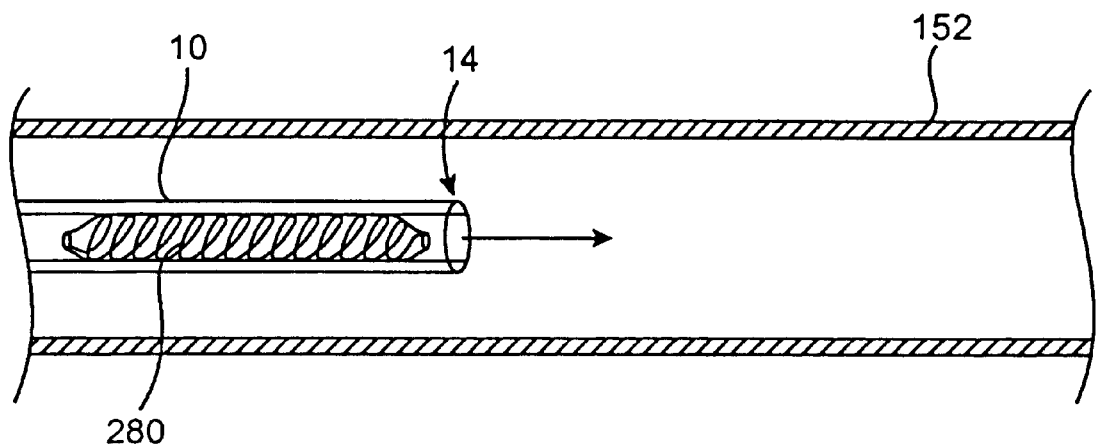
FIG. 24 illustrates a method of deployment or delivery of a blockage device.

Further embodiments of the obstructive device 150 are comprised of a blockage device 280 having no ports through which aspiration of the isolated lung tissue segment may be achieved. After the blockage device 280 is deployed and anchored within a lung passageway 152 leading to a lung tissue segment, the device 280 is to be left as an implant to obstruct the passageway 152 from subsequent airflow. Although the previously described embodiments of obstructive devices 150 having inlet and/or outlet ports 172, 174 may be utilized in a similar manner, the blockage device 280 may not be later accessed to aspirate the lung tissue segment through the device. An example of such a blockage device 280 is illustrated in FIGS. 24 and 25.

As with the previous obstructive devices, the blockage device 280 may be housed within the access catheter 10 or within a catheter that may be passed through the access catheter 10. As depicted in FIG. 24, the obstructive device 150 may be compressed or collapsed within an interior lumen of the access catheter 10. The blockage device 280 depicted is one of many designs which may be utilized. The blockage device 280 may then be pushed out of the distal end 14 of the catheter 10, in the direction of the arrow, into the lung passageway 152. The device 280 is to be self-expanding by tension or shape-memory so that it will expand and anchor itself in the passageway 152.

Figure 25:
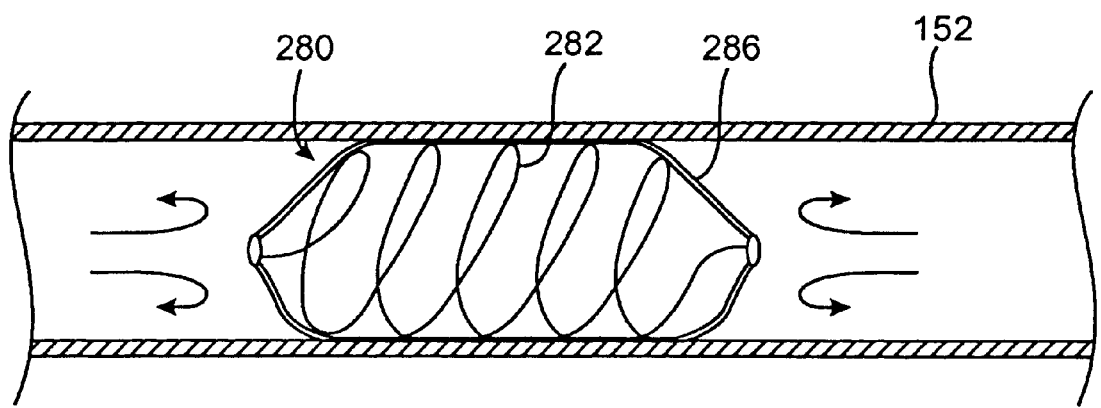
FIG. 25 illustrates an embodiment of a blockage device comprising a coil encased in a polymer film.
Figure 26:
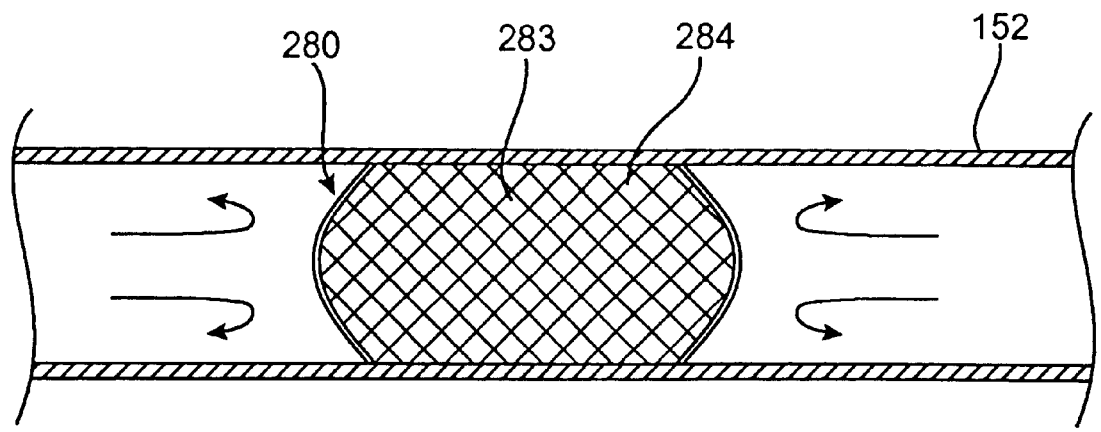
FIG. 26 illustrates an embodiment of a blockage device comprising a mesh connected to a polymer film.

Referring to FIG. 25, one embodiment of the blockage device 280 comprises a coil 282. The coil 282 may be comprised of any type of wire, particularly superelastic or shape-memory wire, polymer or suitable material. The tension in the coil 282 allows the device 280 to expand to fill the passageway 152 and rest against the walls of the passageway 152 to anchor the device 280. In addition, the coil 282 may be connected to a thin polymer film 284, such as webbing between the coils, to seal against the surface of the lung passageway 152. Such a film 284 prevents flow of gases or liquids through the coils, thereby providing an obstruction. Alternatively, as depicted in FIG. 25, the coil 282 may be encased in a sack 286. Expansion of the coil 282 within the sack 286 presses the sack 286 against the walls of the passageway 152 forming a seal. Again, this prevents flow of gases or liquids, depicted by arrows, through the coil 282, thereby providing an obstruction. Similarly, as depicted in FIG. 26, another embodiment of the blockage device 280 comprises a mesh 283. The mesh 283 may be comprised of any type of wire, particularly superelastic or shape-memory wire, polymer or suitable material. The tension in the mesh 283 allows the device 280 to expand to fill the passageway 152 and rest against the walls of the passageway 152 to anchor the device 280. In addition, the mesh 283 may be connected to a thin polymer film 284, such as webbing between the lattice of the mesh, to seal against the surface of the lung passageway 152. Such a film 284 prevents flow of gases or liquids through the mesh, thereby providing an obstruction.

Figure 27:
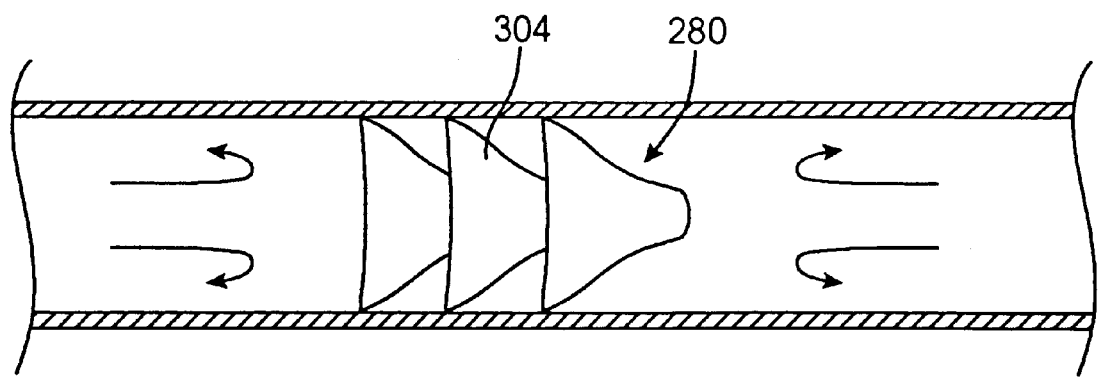
FIG. 27 illustrates an embodiment of a blockage device comprising a barb-shaped structure.

Referring now to FIG. 27, another embodiment of the blockage device 280 comprises a barb-shaped structure 304 designed to be wedged into a lung passageway 152 as shown. Such a structure 304 may be comprised of a solid material, an inflatable balloon material, or any material suitable to provide a blockage function. The structure 304 may be inflated before, during or after wedging to provide sufficient anchoring in the lung passageway. Similarly, the structure 304 may be impregnated or infused with an adhesive or sealant before, during or after wedging to also improve anchoring or resistance to flow of liquids or gasses through the passageway 152.

Figure 28:
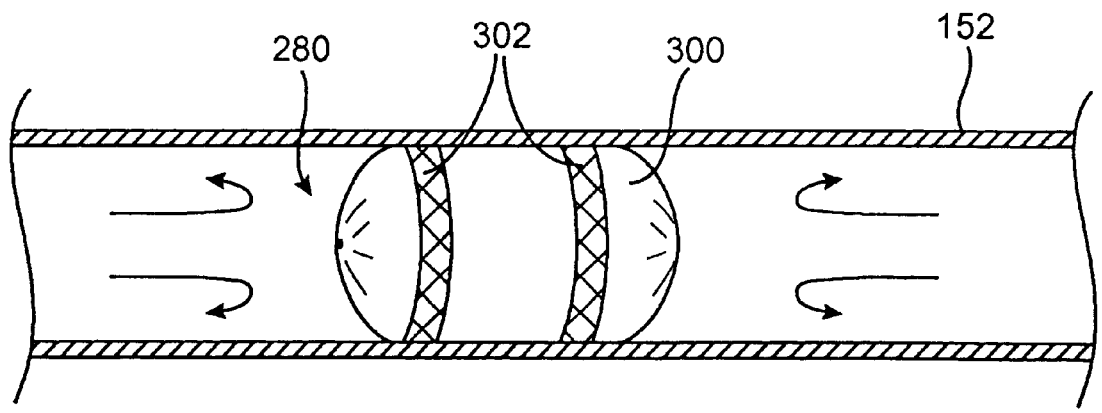
FIG. 28 illustrates an embodiment of a blockage device having a cylindrical-type balloon with textured friction bands.

Referring to FIG. 28, another embodiment of the blockage device 280 comprises an inflated balloon. Such a balloon may take a number of forms. For example, the balloon may have take a variety of shapes, such as round, cylindrical, conical, dogboned, or multi-sectional, to name a few. Or, a series of distinct or interconnected balloons may be utilized. Further, the surface of the balloon may be enhanced by, for example, corrugation or texturing to improve anchoring of the balloon within the lung passageway. FIG. 28 illustrates a cylindrical-type balloon 300 with textured friction bands 302 which contact the walls of the lung passageway 152 when the balloon 300 is inflated as shown.

Figure 29:
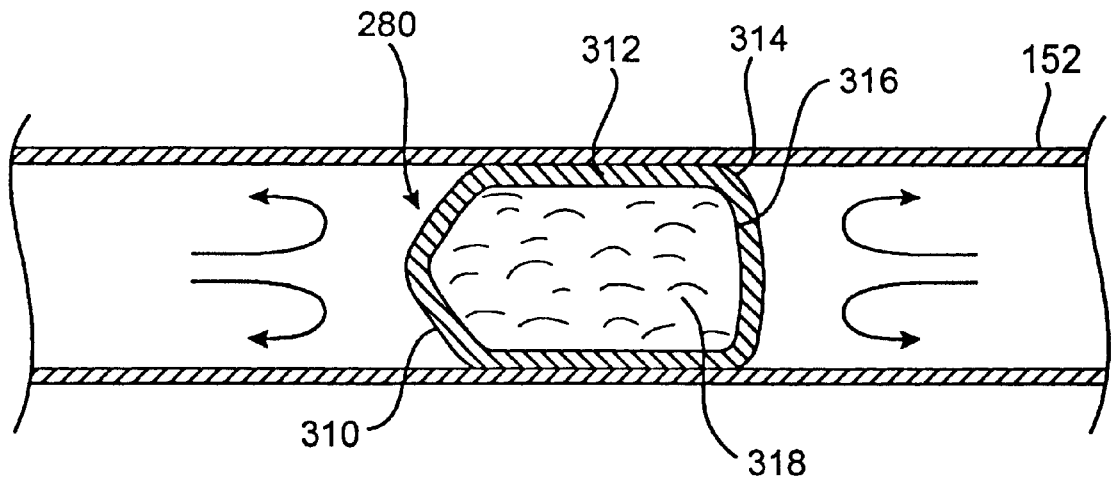
FIG. 29 depicts an embodiment of a blockage device comprising a multi-layer balloon which has an adhesive material between an outer layer and an inner layer of the balloon.
Figure 30:
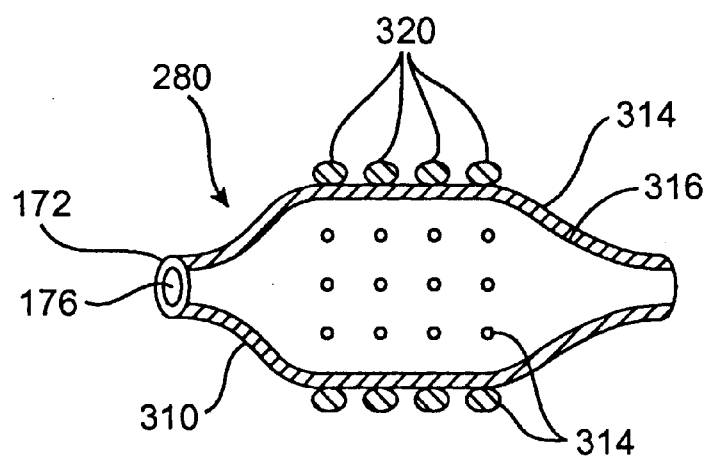
FIG. 30 illustrates an embodiment of a blockage device which is similar to that of FIG. 29, including openings in the outer layer through which adhesive may seep.

It may be appreciated that such balloons may be inflated with an number of materials, including saline, gas, suitable liquids, expanding foam, and adhesive, to name a few. Further, a multi-layer balloon 310 may be utilized, as shown in FIG. 29, which allows the injection of adhesive 312 or suitable material between an outer layer 314 and an inner layer 316 of the balloon 310. Such adhesive 312 may provide a hardened shell on the obstruction device 280 to improve its obstruction abilities. As shown, the balloon 310 may be inflated within the inner layer 316 with a foam 318 or other material. Similarly, as shown in FIG. 30, the outer layer 314 of the blockage device 280 may contain holes, pores, slits or openings 320 which allow the adhesive 312 to emerge through the outer layer 314 to the outside surface of the multi-layer balloon 310. When the balloon 310 is inflated within a lung passageway 152, the outer layer 314 of the balloon 310 will press against the walls of the passageway 152 and the adhesive 312 will bond with the walls in which it contacts. Such adhesion is designed to improve anchorage and obstructive abilities of the blockage device 280.

It may also be appreciated that the above described blockage devices may be impregnated, coated or otherwise deliver an antibiotic agent, such as silver nitrate. Such incorporation may be by any means appropriate for delivery of the agent to the lung passageway. In particular, a multi-layer balloon may be provided which allows the injection of an antibiotic agent between an outer layer and an inner layer of the balloon 310. As previously described and depicted in FIG. 30, the outer layer 314 of the blockage device 280 may contain holes, pores, slits or openings 320 which allow the agent to emerge through the outer layer 314 to the outside surface of the multi-layer balloon 310. Thus, the agent may be delivered to the walls and/or the lung passageway.

It may further be appreciated that the blockage device 280 may comprise a variety of designs having various lengths and shapes. In addition, many of the designs illustrated for use as a blockage device 280 may also be adapted with an aspiration port for use as described in relation to the previously illustrated embodiments of obstruction devices 150. For example, such a port 172 having a septum 176 is shown in FIG. 30. If the port is not accessed, the device simply serves as a blockage device 280. Thus, in some cases, blockage devices 280 and obstructive devices 150 are synonymous.

Figure 31:
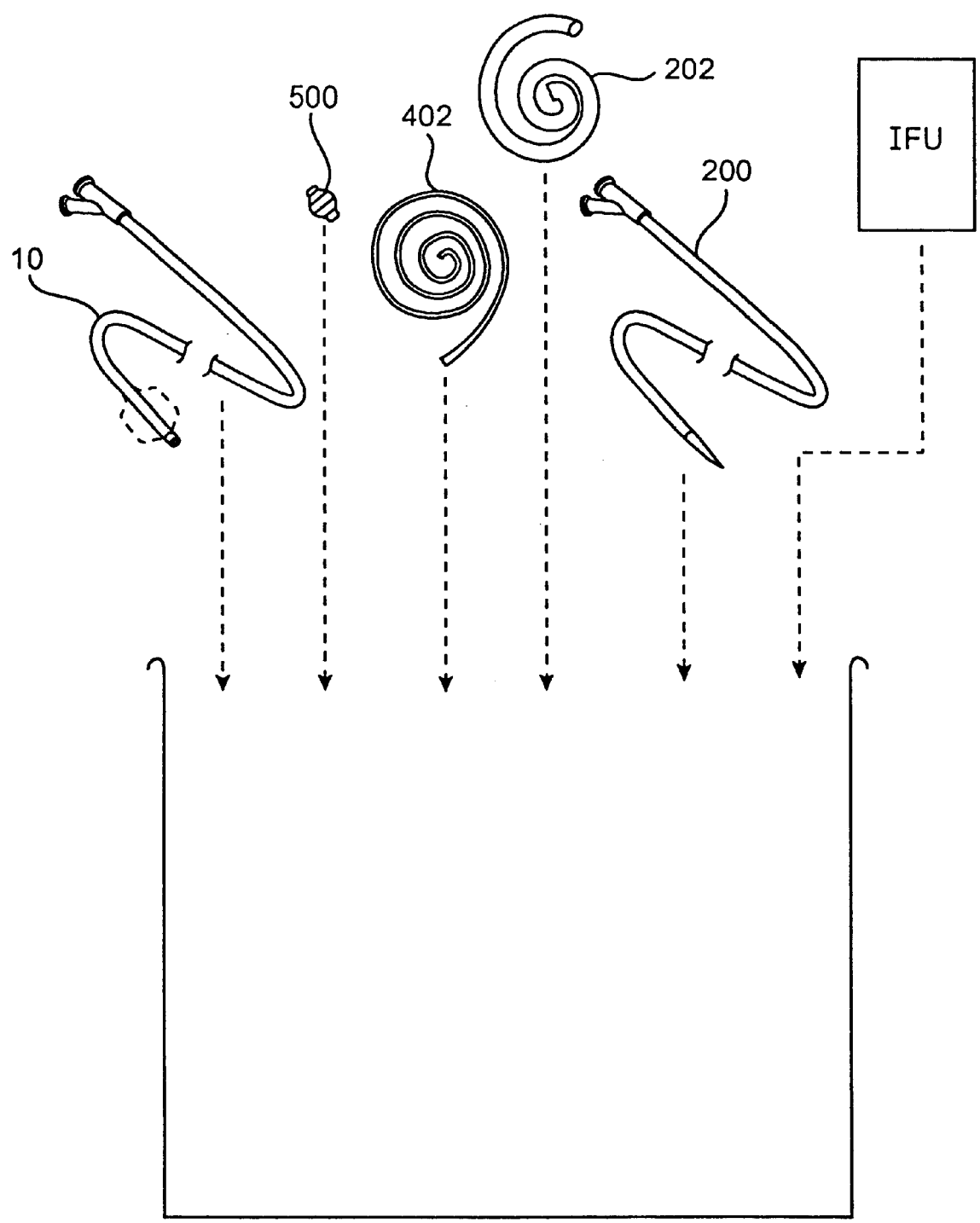
FIG. 31 illustrates a kit constructed in accordance with the principles of the present invention.

Referring now to FIG. 31, kits 400 according to the present invention comprise at least an obstruction or blockage device 500 and instructions for use IFU. Optionally, the kits may further include any of the other system components described above, such as an access catheter 10, guidewire 402, access tube 200, aspiration catheter 202 or other components. The instructions for use IFU will set forth any of the methods as described above, and all kit components will usually be packaged together in a pouch 450 or other conventional medical device packaging. Usually, those kit components which will be used in performing the procedure on the patient will be sterilized and maintained sterilely within the kit. Optionally, separate pouches, bags, trays, or other packaging may be provided within a larger package, where the smaller packs may be opened separately and separately maintain the components in a sterile fashion.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for lung volume reduction, said method comprising:
    deploying an obstructive device in a lung passageway to a lung tissue segment; and
    aspirating the segment through the deployed obstructive device to at least partially collapse the lung segment.

2. A method as in claim 1, wherein aspirating comprises coupling an aspiration catheter to the obstructive device and aspirating gas through the catheter from the segment.

3. A method as in claim 2, wherein the obstructive device comprises an inlet port, the aspiration catheter comprises an access tube and coupling comprises passing an access tube through the inlet port.

4. A method as in claim 3, wherein the inlet port comprises a self-sealing septum and coupling comprises piercing the access tube through the septum.

5. A method as in claim 4, wherein the septum comprises a solid membrane or a pre-cut membrane.

6. A method as in claim 2, wherein the obstructive device comprises a valve and coupling comprises engaging the aspiration catheter to the valve, wherein aspiration opens the valve.

7. A method as in claim 1, wherein aspirating comprises:
    advancing an aspiration catheter into the lung passageway toward the obstructive device, wherein the aspiration catheter has an occlusion balloon near its distal end;
    inflating the occlusion balloon to substantially occlude the lung passageway proximal to the obstructive device; and
    aspirating gas through the obstructive device and the catheter.

8. A method as in claim 7, wherein the obstructive device comprises a valve and aspirating opens the valve.

9. A method as in claim 8, wherein the valve comprises a port and engaging comprises sliding a coupling member or the aspiration catheter over the port to form a seal.

10. A method as in any of claims 1, 3 or 6, wherein the obstructive device comprises a structural support and deploying comprises expanding the structural support so that it anchors in the passageway.

11. A method as in claim 10, wherein the structural support comprises a self-expanding support and expanding comprises releasing the self-expanding support from constraint so that it expands and thereby anchors in the passageway.

12. A method as in claim 11, wherein deploying further comprises inflating a balloon which expands the structural support.

13. A method as in claim 1, further comprising positioning an access catheter in the lung passageway prior to deployment of the obstruction device, said access catheter having a proximal end, a distal end, and at least one lumen extending therethrough.

14. A method as in claim 13, wherein the access catheter has an occlusion balloon near its distal end and aspirating comprises:

inflating the occlusion balloon to substantially occlude the lung passageway proximal to the obstructive device; and aspirating gas through the obstructive device and the catheter.

15. A method as in claim 14, wherein the access catheter provides optical imaging.

16. A method as in claim 14, wherein the access catheter is steerable.

17. A method as in claim 14, wherein the access catheter is positioned with the use of a guidewire.

18. A method as in claim 17, wherein the guidewire provides imaging capabilities.

19. A method as in claim 1, further comprising introducing a gas or liquid to the segment prior to aspiration.

20. A method as in claim 19, wherein the gas comprises 100% oxygen, a Helium-Oxygen mixture or a low molecular weight gas.

21. A method as in claim 19, wherein the liquid comprises perfluorocarbon or a drug.

22. A method for lung volume reduction, said method comprising deploying a unidirectional valve within a lung passageway to a lung tissue segment, wherein the valve opens during expiration to allow outflow of gas from the lung segment and the valve closes during inspiration to prevent inflow of gas to the lung segment.

23. A method as in claim 22, wherein the unidirectional valve comprises a port covered by a flexible layer which is attached to the port by at least one point of connection.

24. A method as in claim 23, wherein at least a portion of the flexible layer moves away from the port during expiration to allow outflow of gas through the port and moves against the port during inspiration to prevent inflow of gas through the port.

25. A method as in claim 24, wherein the flexible layer is solid and outflow of gas through the port during expiration flows between the points of connection and around the edges of the flexible layer.

26. A method as in claim 24, wherein the flexible layer has holes and the port further comprises a partition having holes which are not aligned with the layer holes so that at least a portion of the flexible layer moves away from the partition during expiration to allow outflow of gas through the partition holes and the layer holes and the layer moves against the partition during inspiration to prevent inflow of gas through the holes.

27. A method as in claim 26, further comprising positioning an access catheter in the lung passageway prior to deployment of the obstructive device, said access catheter having a proximal end, a distal end, and at least one lumen extending therethrough.

28. A method as in claim 27, wherein the access catheter provides optical imaging.

29. A method as in claim 27, wherein the access catheter is steerable.

30. A method as in claim 27, wherein the access catheter is positioned with the use of a guidewire.

31. A method as in claim 30, wherein the guidewire provides imaging capabilities.

32. A method for lung volume reduction, said method comprising:

accessing a lung passageway to a lung tissue segment; and deploying a blockage device in the passageway.

33. A method as in claim 32, wherein the blockage device comprises a structural support and a sack.

34. A method as in claim 33, wherein the structural support comprises a coil or mesh.

35. A method as in claim 33, wherein the structural support is connected to the sack.

36. A method as in claim 33, wherein the structural support is encased in the sack.

37. A method as in claim 32, wherein the blockage device comprises an inflatable member and further comprising inflating the inflatable member.

38. A method as in claim 37, wherein the inflatable member comprises a multi-layer balloon having an outer layer and an inner layer and inflation comprises injecting a first material within the inner layer.

39. A method as in claim 38, further comprising injecting a second material in an area between the inner and outer layers.

40. A method as in claim 39, wherein the outer layer has openings and injection of the second material provides flow of the second material through the openings.

41. A method as in claim 32, wherein accessing a lung passageway comprises positioning a catheter in the lung passageway.

42. A method as in claim 41, wherein the catheter is an access catheter having a proximal end, a distal end, and at least one lumen extending therethrough.

43. A method as in claim 42, wherein the access catheter provides optical imaging.

44. A method as in claim 41, wherein the access catheter is steerable.

45. A method as in claim 41, wherein the access catheter is positioned with the use of a guidewire.

46. A method as in claim 45, wherein the guidewire provides imaging capabilities.

47. A method as in claim 32, further comprising introducing 100% oxygen, Helium-Oxygen mixture or low molecular weight gas to the segment prior to deploying the blockage device in the passageway.

48. A device for obstructing and bleeding gas from a lung tissue segment, said device comprising:

an expandable structure which is deployable within a lung passageway; and means for the expandable structure for blocking airflow in one direction therethrough and permitting airflow in the other direction therethrough.

49. A device as in claim 48, wherein the blocking means comprises a valve.

50. A device as in claim 49, wherein the valve is biased to open in response to expiration and remain closed in response to inspiration.

51. A device as in claim 49, wherein the valve is biased to open in response to an aspiration vacuum applied by an aspiration catheter.

52. A device as in claim 51, further comprising a port for selectively coupling to an aspiration catheter.

53. A device as in claim 48, wherein the blocking means comprises a self-sealing septum, wherein a penetrating element on an aspiration catheter can be selectively penetrated through the septum to draw air therethrough.

54. A device as in claim 48, wherein the expandable structure comprises superelastic, shape-memory or spring tempered wire so that the expandable structure is self-expanding.

55. A device as in claim 54, wherein the expandable structure comprises a coil.

56. A device as in claim 54, wherein the expandable structure comprises radial segments which allow the device to expand and longitudinal segments which rest against the lung passageway.

57. A system for obstructing a lung passageway to a lung tissue segment, said system comprising:

an access catheter having a proximal end, a distal end, and at least one lumen extending therethrough, and an obstruction device deployable within the lung passageway having an inlet port adapted for aspirating the lung tissue segment through the inlet port, wherein the obstruction device is introduceable by the access catheter.

58. A system as in claim 57, wherein the obstruction device is houseable within a lumen of the access catheter for deployment out of its distal end.

59. A system as in claim 57, wherein the obstruction device is mountable on the access catheter near its distal end.

60. A kit comprising:

an obstruction device deployable within a lung passageway; and instructions for use according to a method of lung volume reduction comprising:

deploying an obstructive device in a lung passageway to a lung tissue segment; and aspirating the segment through the deployed obstructive device to at least partially collapse the lung segment.

61. A kit as in claim 60, further comprising an access catheter having a proximal end, a distal end, and at least one lumen extending therethrough.

62. A kit as in claim 61, wherein the access catheter provides optical imaging.

63. A kit as in claim 60, further comprising a guidewire.

64. A kit as in claim 63, wherein the guidewire provides optical imaging.

65. A kit as in claim 60, further comprising an access tube.

66. A kit as in claim 60, further comprising an aspiration catheter.

67. A kit comprising:

an obstruction device deployable within the lung passageway; and instructions for use according to a method of lung volume reduction comprising deploying a unidirectional valve within a lung passageway to a lung tissue segment, wherein the valve opens during expiration to allow outflow of gas from the lung segment and the valve closes during inspiration to prevent inflow of gas to the lung segment.

68. A kit comprising:

an obstruction device deployable within the lung passageway; and instructions for use according to a method of lung volume reduction comprising:

accessing a lung passageway to a lung tissue segment; and deploying a blockage device in the passageway.

* * * * *